United States Patent
Weissbach et al.

(10) Patent No.: US 7,414,139 B2
(45) Date of Patent: Aug. 19, 2008

(54) CATALYTIC ANTIOXIDANTS AND METHODS OF USE

(75) Inventors: Herbert Weissbach, Boynton Beach, FL (US); Nathan Brot, West Orange, NJ (US)

(73) Assignees: Florida Atlantic University, Boca Raton, FL (US); Hosptial for Special Surgery, New York, NY (US)

( * ) Notice: Subject to any disclaimer, the term of this patent is extended or adjusted under 35 U.S.C. 154(b) by 0 days.

(21) Appl. No.: 11/512,616

(22) Filed: Aug. 29, 2006

(65) Prior Publication Data

US 2007/0072935 A1    Mar. 29, 2007

Related U.S. Application Data

(62) Division of application No. 10/723,809, filed on Nov. 26, 2003, now Pat. No. 7,129,374.

(60) Provisional application No. 60/429,269, filed on Nov. 26, 2002.

(51) Int. Cl.
*C07D 209/44* (2006.01)
*C07D 209/04* (2006.01)
*C07D 305/14* (2006.01)
*C07D 307/02* (2006.01)
*C07D 305/12* (2006.01)

(52) U.S. Cl. .................. 548/470; 548/469; 549/263; 549/295; 549/320; 549/321; 549/324

(58) Field of Classification Search .................. None
See application file for complete search history.

(56) References Cited

U.S. PATENT DOCUMENTS

| 5,053,429 A | 10/1991 | Hirsch et al. |
| 5,401,774 A | 3/1995 | Pamukcu et al. |
| 5,608,067 A * | 3/1997 | Afonso et al. .................. 546/82 |

OTHER PUBLICATIONS

Minetti et al. "Reduction of Dabs-L0Methionine-dl Sulfoxide by Protein Methionine Sulfoxide Reductase from Polymorphonuclear Leukocytes: Stereospecificity towards the I-Sulfoxide", Ital. J. Biochem., (1994), vol. 43, pp. 273-283.
Girmaud et al. "Repair of Oxidized Proteins", J. Biol. Chem., (2001), vol. 276, pp. 48915-48920.
Rahman et al. "High Level Expression and Purification of Peptide Methionine Sulfoxide Reductase in *Escherichia coli*", Cellular & Molecular Biol., (1992), vol. 38, pp. 529-542.

(Continued)

*Primary Examiner*—Yvonne Eyler
*Assistant Examiner*—Yevegeny Valenrod
(74) *Attorney, Agent, or Firm*—Darby & Darby PC; Nicholas A. Zachariades

(57) ABSTRACT

The invention provides small molecules that act as catalytic antioxidants and methods of use thereof. The compounds can repeatedly bind and destroy reactive oxygen species by serving as substates for enzymes of the methionine sulfoxide reductase (Msr) class. Some embodiments of the catalytic antioxidant compounds are derived from drugs with anti-inflammatory activity due to inhibition of cyclooxygenase enzymes.

9 Claims, 13 Drawing Sheets

OTHER PUBLICATIONS

Etienne et al. "A Methionine Sulfoxide Reductase in *Escherichia coli* that Reduces the R Enantiomer of Methionine Sulfoxide", Biochem. & Biophys. Res. Comm., (2003), vol. 300, pp. 378-382.

Spector et al. "New Membrane-associated and Soluble Peptide Methionine Sulfoxide Reductases in *Escheirchia coli*", Biochem. & Biophys. Res. Comm., (2003), vol. 302, pp. 284-289.

Kita et al. "Enantioselective Total Synthesis of a Potent Antitumor Antibiotic, Fredericamycin A", J. Am. Chem. Soc., (2001), vol. 123, pp. 3214-3222.

Fukuyama et al. "Stereocontrolled Synthesis of (−)-Hapalindole G", J. Am. Soc., (1994), vol. 116, pp. 3125-3126.

Conte et al. "Asymmetric Oxidation of Thioethers. Enantioselective Synthesis of beta-Hydroxysulfoxides by Direct Oxidation", Tetrahedron Lett., (1989), vol. 30, pp. 4859-4862.

O'Donnell et al. "The Stereoselective Synthesis of alpha-Amino Acids by Phase-Transfer Catalysis", J. Am. Chem. Soc., (1989), vol. 111, pp. 2353-2355.

Hartley et al. "Complex I Inhibitors Induce Dose-Dependent Apoptosis in PC12 Cells".

Rosen et al. "Mutations in Cu/Zn Superoxide Dismutase Gene are Associated with Familial Amyotrophic Lateral Scierosis", Natuer, (1993), vol. 362, pp. 59-62.

Weissbach et al. "Peptide Methionin Sulfoxide Reductase: Structure, Mechanism of Action, and Biological Function", Archives of Biochem. & Biophys., (2002), vol. 397, No. 2, pp. 172-178.

Moskovitz et al. "Methionine Sulfoxide Reductase (MsrA) is a Regulator of Antioxidant Defense and Lifespan in Mammals", PNAS, (2001), vol. 98, No. 23, pp. 12920-12925.

Ruan et al . "High-Quality Life Extension by the Enzyme Peptide Methionine Sulfoxide Reductase", PNAS, (2002), vol. 99, No. 5, pp. 2748-2753.

Ejiri et al. "The Purfication of Methionine Sulfoxide Reductase from *Escherichia coli*", Anal. Biochem., (1980), vol. 102, pp. 393-398.

Brot et al. "Reduction of N-Acetyl Methionine Sulfoxide: A Simple Assay for Peptide Methionine Sulfoxide Reductase", Anal. Biochem., (1982), vol. 122, pp. 291-294.

Moskovitz et al. "Cloning and Expression of a Mammalian Gene Involoved in the Reduction of Methionine Sulfoxide Residues in Proteins", Proc. Natl. Acad. Sci., (1996), vol. 93, pp. 2095-2099.

* cited by examiner

CATALYTIC ANTIOXIDANTS AND METHODS OF USE

CROSS REFERENCE TO RELATED APPLICATION

The present application is a divisional application of U.S. Ser. No. 10/723,809 filed Nov. 26, 2003, now allowed, which claims the priority of U.S. provisional application No. 60/429,269 filed on Nov. 26, 2002, which are incorporated herein by reference in their entirety.

STATEMENT AS TO FEDERALLY SPONSORED RESEARCH

Not applicable.

FIELD OF THE INVENTION

The invention relates to the fields of biochemistry, pharmacology, and medicine. More particularly, the invention relates to methods and compositions for promoting health and increasing longevity by reducing oxidative damage to cells and tissues.

BACKGROUND

Oxygen is involved in a wide range of normal metabolic reactions and is essential for the survival of all aerobic organisms, including human beings. Reactive oxygen species (ROS), such as superoxide, are produced in abundance as a byproduct of the incomplete reduction of oxygen that has entered the respiratory chain. Superoxide is the precursor of other damaging oxygen species including hydrogen peroxide, the hypochlorite ion and the hydroxyl radical. Oxidase enzymes in cells such as phagocytes and nitric oxide synthases are other sources of ROS.

While low levels of ROS are present under normal physiological conditions, in excess, ROS can cause oxidative damage to cells and tissues by, for example, oxidizing cellular macromolecules such as nucleic acids, lipids and proteins. Cumulative damage to cells in this manner can result in pathology. Not surprisingly then, oxidative damage has been implicated in a wide variety of diseases and conditions including chronic obstructive lung disorders such as smoker's emphysema, reperfusion damage, neurodegenerative diseases such as Alzheimer's disease, Parkinson's disease, and amyotrophic lateral sclerosis (ALS), heart attacks, stroke, several autoimmune diseases, and aging.

Regarding the latter, oxidative damage to cellular macromolecules has been postulated to accelerate the aging process and shorten lifespan. For example, the level of oxidized methionine in proteins in an animal has been observed to increase with the age of the animal. Moreover, in *Drosophila*, greater resistance to ROS via over-expression of superoxide dismutase and catalase has been correlated with longer lifespan, whereas genetic disruption of superoxide dismutase and catalase has been correlated with shorter lifespan.

Although cells have evolved their own enzymatic antioxidant systems (e.g., superoxide dismutase, catalase, and peroxidase) to neutralize ROS, such systems may not function at ideal levels to minimize the rate of aging and the development of disease. Accordingly, there is a clear need for non-naturally occurring compositions and methods that reduce oxidative damage to cells. One approach to increase the antioxidant activity in cells is to provide cells with compounds that directly scavenge ROS, e.g., vitamins C, E, and A, glutathione, ubiquinone, uric acid, carotenoids, and the like. Such conventional antioxidant compounds, however, lose activity after neutralizing only one or two ROS molecules. They are thus limited by the relatively small quantities of ROS that they can destroy.

SUMMARY

The invention relates to the development of methyl sulfoxide or methyl sulfide containing catalytic antioxidants that can repeatedly be oxidized by a ROS, reduced back to an unoxidized form, and oxidized again by a ROS. Unlike a conventional antioxidant molecule, a single catalytic antioxidant molecule of the invention can neutralize a multitude of different ROS molecules.

The regenerative capacity of the catalytic antioxidant molecules of the invention is based on their ability to act as substrates for the methionine sulfoxide reductase (Msr) class of enzymes. Among the various amino acids found in proteins, methionine (Met) is one of the most susceptible to oxidation. Oxidation of methionine by ROS yields methionine sulfoxide [Met(O)]. The Msr enzymes, including MsrA and MsrB prominent in virtually all cells, including mammalian cells, act as repair enzymes that catalyze the reversal of the oxidation reaction, reducing Met(O) back to methionine. In addition to reducing methionine, MsrA and several other forms of Msr enzymes known in bacteria can reduce a variety of other substrates, but in all cases the core functional group recognized by the enzymes is a methyl sulfoxide moiety. By reducing methyl sulfoxide moieties back to methyl sulfide, the Msr enzymes repair damaging oxidation reactions to methionine in proteins. In addition the methionine residues in proteins, via cyclic oxidation and reduction by the Msr system, can act as scavengers of ROS. In these ways the Msr system is believed to contribute to the longevity and health of cells by conferring resistance to ROS (reviewed in Weissbach et al., Archiv. Biochem. Biophys. 397:172-178, 2002).

The catalytic antioxidants of the invention are small molecules that act as substrates for Msr enzymes. A scheme of interaction of the compounds of the invention with the Msr pathway is shown diagrammatically in FIG. 1. Methyl sulfide groups on the antioxidant compounds can react with reactive oxygen species (ROS) such as superoxide or hydrogen peroxide to form methyl sulfoxides, for example methionine sulfoxide, which occurs in proteins and in the free form in cells. Upon trapping and destruction of the ROS by a catalytic antioxidant compound of the invention, the methyl sulfoxide formed thereon can serve as a substrate for one or more Msr enzymes. Nucleophilic attack of the methyl sulfoxide by a cysteine residue in the Msr enzyme leads to transfer of the oxygen from the compound to the enzyme, reducing the compound back to its unoxidized state (FIG. 1). The compounds, thus regenerated, are available for repeated reuse as antioxidants. Thus, the catalytic antioxidant compounds of the invention function not only as typical ROS scavengers, but also regenerate themselves by harnessing the catalytic action of the Msr enzymes.

Accordingly, in one aspect, the invention features non-naturally occurring (or purified, naturally occurring) compounds including at least one methyl sulfide or methyl sulfoxide moiety, the compounds being a substrate for at least one MsrA enzyme and at least one MsrB enzyme, or a pharmaceutically acceptable salt thereof. Certain embodiments of the compounds are based on a backbone derived from the chemical structure of sulindac (1(Z)-5-fluoro-2-methyl-1[[4-(methylsulfinyl)phenyl)methylene]-1H-indenyl-3-acetic acid).

Other embodiments of the compounds are non-naturally occurring (or purified, naturally occurring) compounds including at least one methyl sulfide or methyl sulfoxide moiety, the compounds being a substrate for at least one Msr enzyme and having a backbone not based on sulindac. Various embodiments of these compounds have a backbone based on several known cyclooxygenase (COX) inhibitors, including acetyl salicylic acid, mefenamic acid, ibuprofen, indomethacin, and rofecoxib (Vioxx®). The invention also includes compositions based on these compounds in a pharmaceutically acceptable carrier.

In another aspect, the invention provides a method for reducing, preventing or reversing oxidative damage in a cell. The method includes the steps of: (a) providing a non-naturally occurring (or purified, naturally occurring) compound including in its chemical structure at least one methyl sulfide or methyl sulfoxide moiety, the compound being a substrate for at least one Msr enzyme; (b) providing a cell expressing at least one Msr enzyme, the cell containing or being exposed to reactive oxygen species; and (c) contacting the cell with an amount of the compound sufficient to reduce, prevent, or reverse oxidative damage in the cell by the reactive oxygen species.

The cell can be within an animal subject, such as a human being. The animal subject can have a condition or disorder associated with oxidative damage. The disorder can involve degeneration of a nerve cell. The condition affecting the subject can be age-related.

Yet another embodiment of the invention is a method for extending the lifespan of an animal. The method involves administering to the animal a therapeutically effective amount of a non-naturally occurring (or purified, naturally occurring) compound including at least one methyl sulfide or methyl sulfoxide moiety, the compound being a substrate for at least one Msr enzyme.

As used herein, the terms "methionine moiety" and "methionine analog" include all structures encompassed by general methionine formula described herein, including selenomethionine derivatives.

As used herein, the term "catalytic antioxidant" refers to a non-naturally occurring (or purified, naturally occurring) antioxidant compound that can be enzymatically regenerated after it is oxidized by an oxidizing agent (for example a ROS) such that each equivalent of antioxidant compound can destroy more than one equivalent of the oxidizing agent.

Unless otherwise defined, all technical terms used herein have the same meaning as commonly understood by one of ordinary skill in the art to which this invention belongs.

Although methods and materials similar or equivalent to those described herein can be used in the practice or testing of the present invention, suitable methods and materials are described below. The particular embodiments discussed below are illustrative only and not intended to be limiting. All publications, patent applications, patents, and other references mentioned herein are incorporated by reference in their entirety. In the case of conflict, the present specification, including definitions will control.

DETAILED DESCRIPTION

The invention encompasses compositions and methods relating to catalytic antioxidants useful in reducing or preventing oxidative damage in cells. The antioxidant compounds contain active sites that capture ROS. The antioxidant ability of the compounds is regenerated following capture of ROS by interaction with enzymes of the Msr class that reduce methyl sulfoxide moieties back to the methyl sulfide.

The below described preferred embodiments illustrate various compositions and methods within the invention. Nonetheless, from the description of these embodiments, other aspects of the invention can be made and/or practiced based on the description provided below.

Biological Methods

Methods involving conventional chemistry, cell biology and molecular biology techniques are described herein. Such techniques are generally known in the art and are described in detail in methodology treatises such as Classics in Total Synthesis. Targets, Strategies Methods, K. C. Nicolaou and E. J. Sorensen, VCH, New York, 1996; and The Logic of Chemical Synthesis, E. J. Coney and Xue-Min Cheng, Wiley & Sons, NY, 1989. Molecular biological and cell biological methods are described in treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Catalytic Antioxidants Having Methyl Sulfide or Methyl Sulfoxide Groups

The invention provides small molecules containing at least one (e.g., 1, 2, 3 or more) methyl sulfoxide or methyl sulfide group that can enter cells and prevent oxidative damage by a catalytic antioxidant mechanism. The methyl sulfide group on the compounds reacts with ROS, forming methyl sulfoxide. The methyl sulfoxide-bearing compounds, in turn, act as substrates for Msr enzymes which reduce the compounds and thereby regenerate their antioxidant properties. These compounds can be administered to cells or animals to reduce cellular damage caused by ROS.

Figure 1:
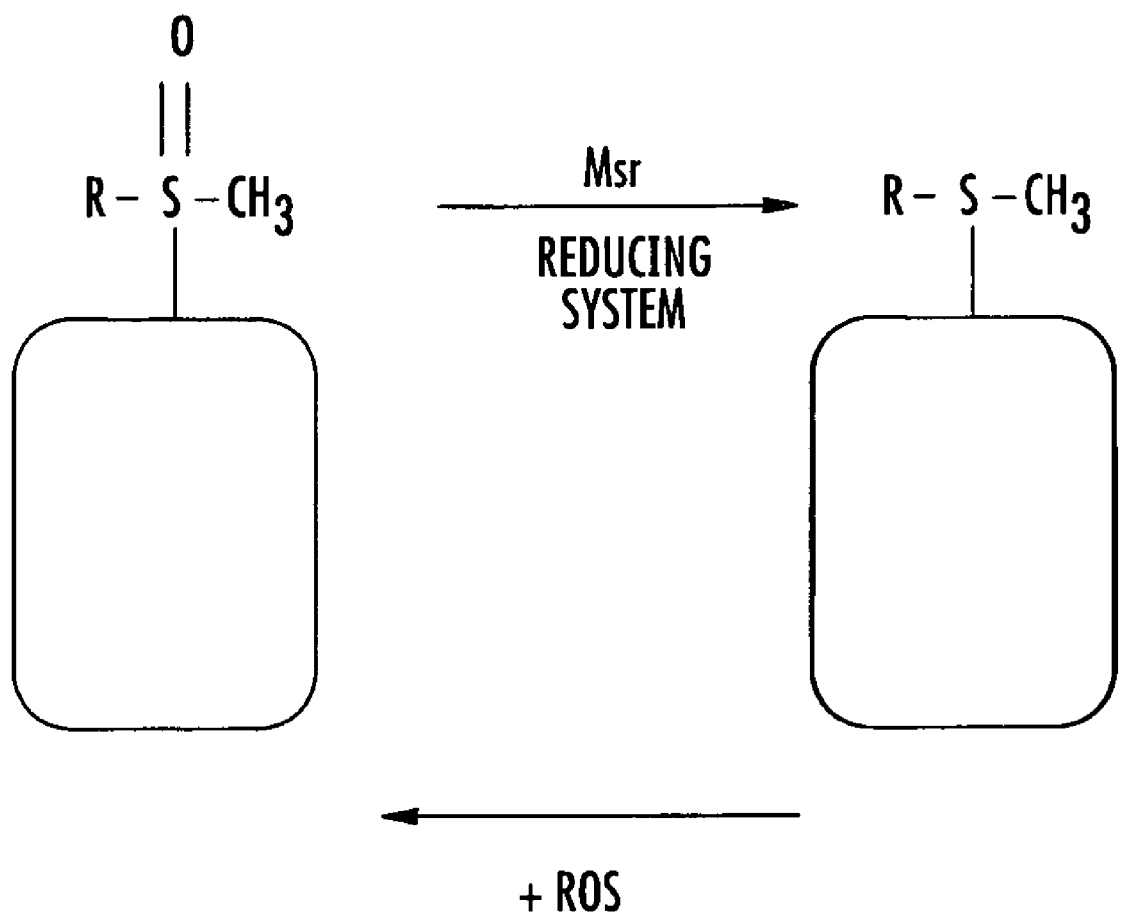
FIG. 1 is a schematic diagram showing the mechanism of action of a catalytic anti-oxidant, according to an embodiment of the invention.

Referring to FIG. 1, these compounds serve 1) as ROS scavengers (antioxidants) by virtue of the active groups within their structures that destroy or react with ROS, and 2) as catalytic antioxidants by acting as substrates for Msr enzymes that reduce the oxidized compounds back to the unoxidized form capable of further reaction with ROS. The catalytic nature of the antioxidant compounds of the invention is due to their ability to serve as substrates for Msr enzymes. The core functional group recognized by these enzymes is methyl sulfoxide. In the case of N-methionine-containing peptide and protein substrates, this functional group is contained within the amino acid methionine.

Figure 2:
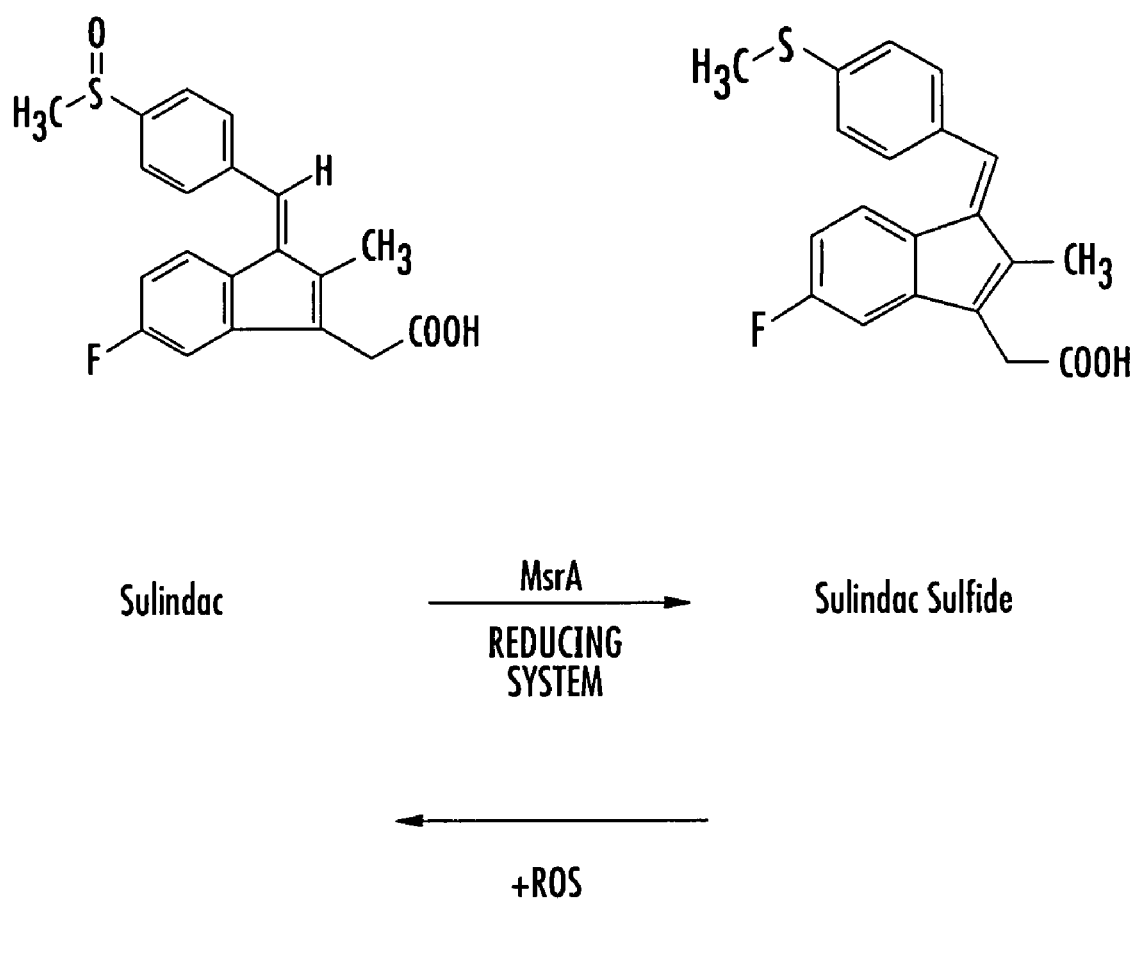
FIG. 2 is a schematic diagram showing the cycle of catalytic antioxidant activity of sulindac, catalyzed by an MsrA enzyme, according to an embodiment of the invention.

Any compound having a methyl sulfide or methyl sulfoxide functional group that is a substrate for a Msr enzyme can be used. Sulindac, a non-steroidal anti-inflammatory drug and COX inhibitor, is one example of a methyl sulfoxide-containing compound that serves as a substrate for Msr enzymes. Sulindac is a pro drug, and is only active as a COX inhibitor when the methyl sulfoxide moiety on the molecule is reduced to the sulfide. Heretofore, sulindac was not known to act as a substrate for a Msr. FIG. 2 shows the reduction of sulindac to sulindac sulfide, catalyzed by Msr. As described below, sulindac was tested as a substrate against six known members of the Msr family identified in bacteria (*E. coli*) and against Msr enzymes present in mammalian (bovine) tissues. MsrA and a membrane-associated Msr of bacteria were shown to be able to reduce sulindac to the active sulfide. In mammalian tissues, reduction of sulindac was primarily attributable to the activity of MsrA.

As further described below, sulindac administration (1) protected *Drosophila* against the damage from paraquat-induced ROS production, (2) prolonged the survival of spinal cord motor neurons in mice with a neurodegenerative disease caused by oxidative damage, and (3) extended the lifespan of the foregoing mice.

Methionine-Based Catalytic Antioxidants

In one aspect, the invention provides catalytic antioxidant compounds having methionine moieties or analogs of methionine. Such compounds are substrates for Msr enzymes that recognize the methyl sulfoxide functional group in methionine (for example, MsrA and MsrB). The methionine moiety or analog found in the methionine-containing embodiments of the compounds has the following general structure:

general methionine formula (1)

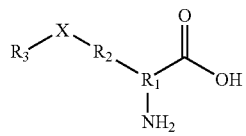

Groups $R_1$, $R_2$, $R_3$, and X in general structure 1 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl, or a fluorinated derivative thereof.

X may be either S or Se in any oxidation state.

As used herein, the terms "methionine moiety" and "methionine analog" include all structures encompassed by general formula 1, including selenomethionine analogs of methionine.

General structure 1 also includes esters and salts of the carboxylic acid. Oligopeptides containing methionine for attachment to small molecules are also encompassed by the invention.

Methionine-Based Catalytic Antioxidants Derived from COX Inhibitors

Inflammation and oxidative damage are known to coexist in many disease states and degenerative conditions. Accordingly, particularly preferred embodiments of the methionine-containing compounds of the invention are derivatives of anti-inflammatory agents such as COX inhibitors. Specific examples of such compounds, employing scaffolds based on several COX inhibitors, and methods for their synthesis are provided in the examples below. Exemplary compounds include those derived from the following scaffolds: sulindac; acetyl salicylic acid (ortho-acetoxybenzoic acid), mefenamic acid (2-[(2,3-Dimethylphenyl)amino]benzoic acid); ibuprofen (α-methyl-4-(2-methylpropyl)-benzeneacetic acid); indomethacin (1-(p-chlorobenzoyl)-5-methoxy-2-methyl-indole-3-acetic acid); and rofecoxib (4-[4-(methylsulfonyl) phenyl]-3-phenyl-2(5H)-furanone, for example, Vioxx®, sold by Merck) and celecoxib (4-[5-(4-methylphenyl)-3-(trifluoromethyl)-1H-pyrazol-1-yl]-benzenesulfonamide, for example, Celebrex® sold by Pfizer.

Embodiments of the invention that are sulindac derivatives can have the following general formulas 2-5:

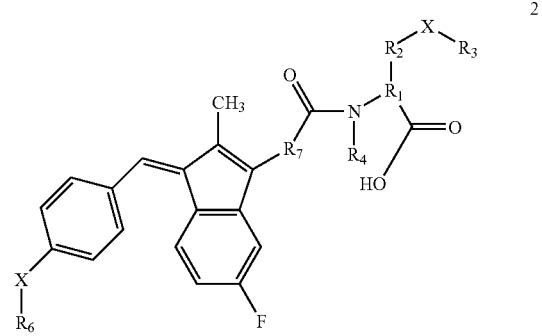

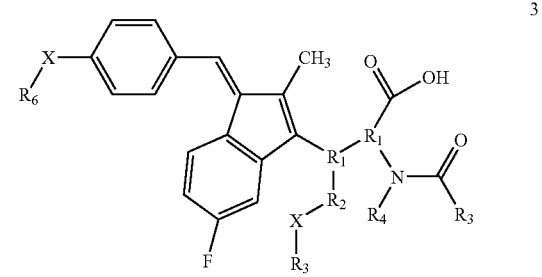

-continued

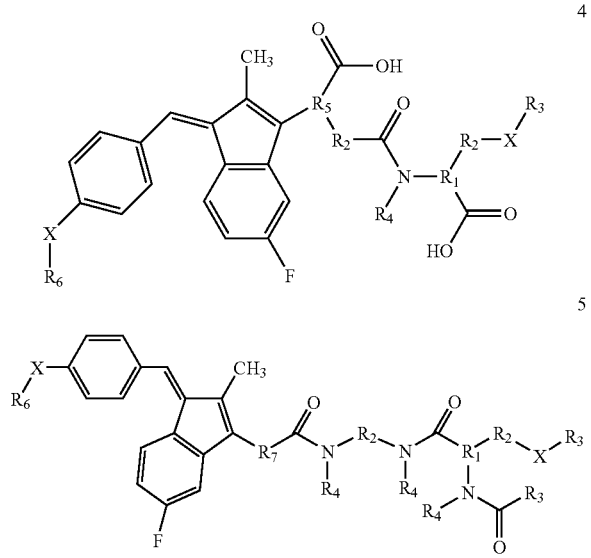

4

5

Groups $R_1$, $R_2$, $R_3$, $R_4$, $R_5$, $R_6$, and X in general formulas 2, 3, 4 and 5 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl, or a fluorinated derivative thereof.

$R_4$ may be a hydrogen or a normal or branched alkyl group having 1 to 6 carbons.

$R_5$ may be a CH (of either R or S configuration).

$R_6$ is a may be a hydrogen or a normal or branched alkyl or fluoroalkyl group having 1 to 6 carbons.

$R_7$ may be a nitrogen (with substituent $R_4$ as defined above), a CH (of either R or S configuration), or a normal or branched alkyl or fluoroalkyl group having 1 to 6 carbons.

X may be either S or Se in any oxidation state.

General structures 2, 3, 4 and 5 also include esters and salts of the carboxylic acid group. The invention also encompasses sulindac derivatives containing oligomeric methionine moieties and analogs.

Embodiments of the invention that are acetyl salicylic acid derivatives can have the following general formula:

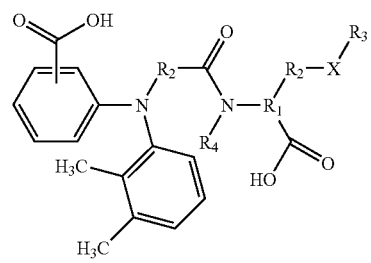

6

The aromatic ring of general structure 6 may contain one or more nitrogen atoms (for example pyridine or pyrazine). The aromatic carboxyl group in general structure 6 may be oriented ortho, meta, or para to the methionine-based moiety. Groups $R_1$, $R_2$, $R_3$, $R_4$, $R_5$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl, or a fluorinated derivative thereof.

$R_4$ may be a hydrogen or a normal or branched alkyl group having 1 to 6 carbons.

$R_5$ may be a nitrogen (with substituent $R_4$ as defined above), an oxygen, or a sulfur.

X may be either S or Se in any oxidation state.

General structure 6 also includes esters and salts of the carboxylic acid group. The invention also encompasses acetyl salicylic acid derivatives containing oligomeric methionine moieties and analogs.

Embodiments of the invention that are mefenamic acid derivatives can have the following general formula:

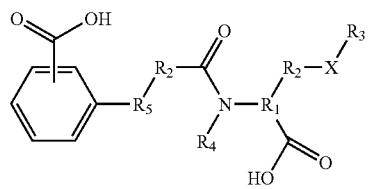

7

Both aromatic rings of general structure 7 may contain one or more nitrogen atoms (for example pyridine or pyrazine). The aromatic carboxyl group in general structure 7 may be oriented ortho, meta, or para to the aniline nitrogen. Groups $R_1$, $R_2$, $R_3$, $R_4$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

X may be either S or Se in any oxidation state.

General structure 7 also includes esters and salts of the carboxylic acid group. The invention also encompasses mefenamic acid derivatives containing oligomeric methionine moieties and analogs.

Embodiments of the invention that are ibuprofen derivatives can have the following general formula:

8

The aromatic ring of general structure 8 may contain one or more nitrogen atoms (for example pyridine or pyrazine). The sec-butyl group in general structure 8 may be oriented ortho, meta, or para to the methionine-based moiety. Groups $R_1$, $R_2$, $R_3$, $R_4$, $R_5$, and X in the general structure are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

$R_5$ may be a CH (of either R or S configuration).

X may be either S or Se in any oxidation state.

General structure 8 also includes esters and salts of the carboxylic acid group. The invention also encompasses ibuprofen derivatives containing oligomeric methionine moieties and analogs.

Embodiments of the invention that are indomethacin derivatives can have the following general formula:

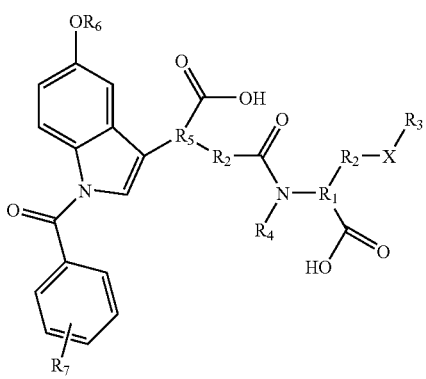

9

Groups $R_1, R_2, R_3, R_4, R_5, R_6, R_7$ and X in general structure 9 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

$R_5$ may be a CH (of either R or S configuration).

$R_6$ is a may be a hydrogen or a normal or branched alkyl or fluoroalkyl group consisting of 1 to 6 carbons.

$R_7$ may be any halogen oriented ortho, meta, or para to the carbonyl group.

X may be either S or Se in any oxidation state.

General structure 9 also includes esters and salts of the carboxylic acid group. The invention also encompasses indomethacin derivatives containing oligomeric methionine moieties and analogs.

Embodiments of the invention that are Vioxx® derivatives can have the following general Formula:

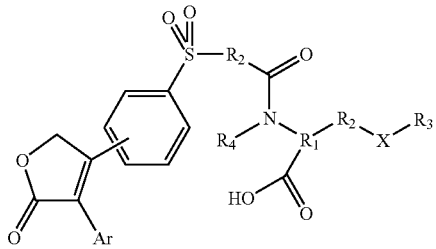

10

The lactone ring in general structure 10 may be oriented ortho, meta, or para to sulfonyl group. Groups $R_1, R_2, R_3, R_4$, and X in general structure 10 are defined as follows:

$R_1$ may be CH (of either R or S configuration).

$R_2$ may be a normal or branched alkyl or fluoroalkyl group having 1 to 6 carbons.

$R_3$ may be ethyl or preferably methyl or a fluorinated derivative thereof.

$R_4$ may be a hydrogen or a normal or branched alkyl group having 1 to 6 carbons.

X may be either S or Se in any oxidation state.

Ar may be phenyl, alkyl and halogen substituted phenyl, and heteroaromatic compounds.

General structure 10 also includes esters and salts of the carboxylic acid group. The invention also encompasses Vioxx® derivatives containing oligomeric methionine moieties and analogs.

Testing of Catalytic Antioxidant Compounds

The ability of any given molecule having a chemical structure including at least one methyl sulfoxide- and/or methyl sulfide-containing moiety, or at least one methionine and/or methionine sulfoxide moiety to act as a catalytic antioxidant can be determined empirically. For example, a molecule containing a methyl sulfoxide group to be tested (i.e., a test molecule) can be subjected to an enzymatic assay that indicates if the test molecule can serve as a substrate for MsrA, MsrB or other members of the Msr family (see, for instance, the NADPH assay described in Example 1, and the extraction assay described in Example 2, below). A test molecule can also be subjected to an assay that indicates the molecule's ability to increase resistance to oxidative stress in cells in vitro (for example PC-12 cells subjected to insult with MPP+) or in an animal subject, for example, Drosophila or a mammalian model of oxidative damage. See, for instance, the assays described in Examples 7, 8 and 9 below.

Preventing/Reversing Oxidative Damage In A Cell

The catalytic antioxidant compounds of the invention can be used to reduce, prevent or reverse oxidative damage in a cell (for example, a cell in an animal). In this method, a non-naturally occurring catalytic antioxidant compound is brought into contact with the cell. After entering the interior of the cell, the compound, if in the reduced (sulfide) form, will be oxidized to the sulfoxide by ROS (i.e., act as a ROS scavenger). Subsequent reduction catalyzed by an Msr enzyme will regenerate the original sulfide. If the test molecule contains a methyl sulfoxide moiety, it will be reduced to the sulfide by the Msr system within the cell and subsequently act as an antioxidant. With either the sulfide or the sulfoxide as the test molecule, the oxidation/reduction cycle will permit the compound to destroy ROS catalytically, as shown in FIG. 1.

The effectiveness of particular compounds can be assessed using conventional in vitro and in vivo assays, for example, determining a cell's, or an animal's response to a challenge with an agent that produces ROS. For instance, to assess a test molecule for the ability to prevent oxidative damage caused by ROS in a cell, cells can be cultured by conventional means and challenged with an agent that produces ROS within the cells. An exemplary cellular system for testing the effect of ROS damage in nerve cells, for example, is an assay employing PC-12 cells subjected to insult with MPP+, an agent that generates superoxide and other oxygen radicals. To assess the efficacy of a test compound in an animal, Drosophila melanogaster (fruit fly) is an excellent animal model. The flies can be treated with an agent that produces ROS (for example, paraquat) and then fed with a diet containing the test molecule and monitored for their survival, compared to control flies receiving Paraquat alone. Mammalian models of oxidative damage are also well known and include inter alia a transgenic mouse model of amyotrophic lateral sclerosis (ALS) based on a mutation in the superoxide dismutase (SOD1) gene.

Animal Subjects

Because oxidative damage to cells is a ubiquitous phenomenon, the invention is believed to be compatible with any animal subject. A non-exhaustive list of examples of such animals includes mammals such as mice, rats, rabbits, goats, sheep, pigs, horses, cattle, dogs, cats, and primates such as monkeys, apes, and human beings. Those animal subjects that have a disease or condition that relates to oxidative damage are preferred for use in the invention as these animals may have the symptoms of their disease reduced or even reversed. In particular, human patients suffering from inflammation, chronic obstructive lung diseases such as emphysema, reperfusion damage after heart attack or stroke, neurodegenerative diseases (for example, Parkinson's disease, Alzheimer's disease, and ALS), autoimmune diseases such as rheumatoid arthritis, lupus, and Crohn's disease, conditions related to premature birth, conditions caused by exposure to ultraviolet light, and age-related conditions (as but one example, age-related degenerative conditions of the eye including age-related macular degeneration and cataract formation) are suitable animal subjects for use in the invention. In the experiments described herein, animals used for demonstration of beneficial effects of protection against ROS damage by the compounds of the invention are the fruit fly and the mouse. Nonetheless, by adapting the methods taught herein to other methods known in medicine or veterinary science (for example, adjusting doses of administered substances according to the weight of the subject animal), the compounds and compositions of the invention can be readily optimized for use in other animals.

Administration of Compositions

The catalytic antioxidant compositions of the invention may be administered to animals including humans in any suitable formulation. For example, the compositions may be formulated in pharmaceutically acceptable carriers or diluents such as physiological saline or a buffered salt solution. Suitable carriers and diluents can be selected on the basis of mode and route of administration and standard pharmaceutical practice. A description of other exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions, or enhance the activity of the Msr system. One such enhancing substance could be nicotinamide which is part of the molecule, NADPH, that supplies the reducing power to the reaction catalyzed by the members of the Msr family.

The compositions of the invention may be administered to animals by any conventional technique. Such administration may be oral or parenteral (for example, by intravenous, subcutaneous, intramuscular, or intraperitoneal introduction). The compositions may also be administered directly to the target site by, for example, surgical delivery to an internal or external target site, or by catheter to a site accessible by a blood vessel. Other methods of delivery, for example, liposomal delivery or diffusion from a device impregnated with the composition, are known in the art. The compositions may be administered in a single bolus, multiple injections, or by continuous infusion (for example, intravenously or by peritoneal dialysis). For parenteral administration, the compositions are preferably formulated in a sterilized pyrogen-free form.

Compositions of the invention can also be administered in vitro to a cell (for example, to prevent oxidative damage during ex vivo cell manipulation, for example of organs used for organ transplantation or in in vitro assays) by simply adding the composition to the fluid in which the cell is contained.

Effective Doses

An effective amount is an amount which is capable of producing a desirable result in a treated animal or cell (for example, reduced oxidative damage to cells in the animal or cell). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for parenteral or oral administration of compositions of the invention would be in the range of about 1 µg to 100 mg/kg of body weight in humans. An effective amount for use with a cell in culture will also vary, but can be readily determined empirically (for example, by adding varying concentrations to the cell and selecting the concentration that best produces the desired result). It is expected that an appropriate concentration would be in the range of about 0.0001-100 mM. More specific dosages can be determined by the method described below.

Toxicity and efficacy of the compositions of the invention can be determined by standard pharmaceutical procedures, using cells in culture and/or experimental animals to determine the $LD_{50}$ (the dose lethal to 50% of the population) and the $ED_{50}$ (the dose that effects the desired result in 50% of the population). Compositions that exhibit a large $LD_{50}/ED_{50}$ ratio are preferred. Although less toxic compositions are generally preferred, more toxic compositions may sometimes be used in in vivo applications if appropriate steps are taken to minimize the toxic side effects.

Data obtained from cell culture and animal studies can be used in estimating an appropriate dose range for use in humans. A preferred dosage range is one that results in circulating concentrations of the composition that cause little or no toxicity. The dosage may vary within this range depending on the form of the composition employed and the method of administration.

EXAMPLES

The present invention is further illustrated by the following specific examples, which should not be construed as limiting the scope or content of the invention in any way.

Example 1

Sulindac is a Substrate For MsrA Enzyme

The enzyme methionine sulfoxide reductase (MsrA) is known to exhibit specificity for substrates that contain a methyl sulfoxide group. This example provides evidence that sulindac, a known antioxidant containing a methyl sulfoxide moiety, can act as a substrate for MsrA.

Materials and Methods.

Reductase assay. With a purified Msr enzyme, sulindac reduction can be measured by a modified NADPH oxidation assay. Reaction mixtures were prepared containing 50 mM Tris-Cl pH 7.4, 15 µg of *E. coli* thioredoxin, 1 µg *E. coli* thioredoxin reductase, 100 nmoles of NADPH, 1 µmole of sulindac and 100-400 ng of MsrA in a final volume of 500 µl. Incubations were performed at 37° C. for various times.

The amount of product (sulindac sulfide) synthesized was determined by measuring the oxidation of NADPH spectrophotometrically at 340 nm. Because sulindac absorbs very strongly at this wavelength, the loss of absorbance at 340 nm could not be measured directly. To accomplish this, the sulindac and sulindac sulfide were removed from the incubations by extraction with ethyl acetate as follows. At the end of incubation, 500 µl of 0.5 M Bis-Tris-Cl pH 5.5 and 3 ml of ethyl acetate were added. The tubes were mixed (vortexed) for 5 seconds (3 times). After separation, the organic phase was removed and another 3 ml of ethyl acetate were added. After mixing the organic phase was again removed. The two extractions essentially removed all of the sulindac and sulindac sulfide, leaving the NADPH in the aqueous phase, which was measured at 340 nm. The loss of absorption at 340 nm, dependent on sulindac, is a measure of sulindac reduction. (Δ0.062 at 340 nm=10 nmoles of sulindac sulfide formed).

Results: The results of a reductase assay using MsrA from E. coli are summarized below in Table 1.

TABLE 1

Reduction of Sulindac to Sulindac Sulfide by MsrA

| Tube # | MsrA (100 ng/µl) | Sulindac (0.2M) | Thioredoxin (5 µg/µl) | MetS(O) (0.2M) | Time (min) | $OD_{340}$ | Δ $OD_{340}$ | Sulindac sulfide (nmol) |
|---|---|---|---|---|---|---|---|---|
| 1 | 8 µl | — | 3 µl | — |  | 0.657 |  | 0 |
| 2 | — | 5 µl | 3 µl | — |  | 0.660 |  | 0 |
| 3 | 1 µl | 5 µl | 3 µl | — | 20 | 0.622 | 0.038 | 5.8 |
| 4 | 2 µl | 5 µl | 3 µl | — | 20 | 0.586 | 0.074 | 11.2 |
| 5 | 4 µl | 5 µl | 3 µl | — | 20 | 0.522 | 0.138 | 21.0 |
| 6 | 2 µl | 5 µl | — | — | 20 | 0.684 |  |  |
| 7 | 2 µl | 5 µl | 3 µl | — | 10 | 0.626 | 0.034 | 5.2 |
| 8 | 2 µl | 5 µl | 3 µl | — | 30 | 0.531 | 0.129 | 19.4 |

The results show that sulindac was reduced in a time- and concentration-dependent manner by MsrA enzyme.

Example 2

Sulindac is a Substrate for Msr Enzymes in Bacteria and Mammals

This example demonstrates that sulindac is a substrate for MsrA and membrane-bound Msr in E. coli and for MsrA and possibly other Msr enzymes in mammalian tissues.

Material and Methods.

Chemicals, enzymes and substrates. Sulindac (S), sulindac sulfide (SS) and all chemicals and E. coli thioredoxin reductase were obtained from Sigma Chemicals (St. Louis, Mo.), unless noted otherwise. Thioredoxin (from E. coli) was purchased from Promega (Madison, Wis.). N-acetyl-$^3$H-met-R, S—(O), met-R—(O), met-S—(O) DABS-met-R—(O) and DABS-met-S—(O) were prepared as previously described (Brot N. et al., Anal. Biochem. 122 (1982) 291-294; Lavine, F. T. J. Biol. Chem. 169 (1947) 477-491; Minetti G. et al., Ital. J. Biochem. 43 (1994) 273-283).

Bacterial enzymes. Recombinant MsrA and MsrB from Escherichia coli were obtained as described previously (Grimaud, R.et al., J. Biol. Chem. 276 (2001) 48915-48920; Rahman, M. A. et al., Cellular & Molecular Biology 38 (1992) 529-542). Partially purified DEAE fractions of free-S-Msr (fSMsr), free-R Msr (fRMsr) and MsrA1, and a membrane vesicle associated Msr (mem-R,S-Msr) were prepared from an E. coli MsrA/B double mutant as described (Etienne, F. et al., Biochem. & Biophys. Res. Comm. 300 (2003) 378-382; Spector, D. et al., Biochem. & Biophys. Res. Comm. 302 (2003) 284-289). The enzyme preparations had specific activities similar those reported earlier.

Mammalian enzymes. Calf liver, kidney and brain extracts were prepared at 4° C. Thirty grams each of calf tissue (liver, kidney, brain) were minced using a hand-held homogenizer in 5 volumes of buffer A containing 250 mM sucrose, 10 mM Tris-Cl pH 7.4 and 1 mM EDTA. The homogenates were dounced (6 strokes) and spun at 1,500×g for 10 minutes and the pellet was discarded. The supernatants (S-10) were spun at 10,000×g for 10 minutes. The S-10 supernatants were centrifuged at 100,000×g for 12 hours and the resulting pellets and supernatants (S-100) were saved. The S100 pellets were suspended in cold buffer A and centrifuged at 100,000×g for 4 hours. The washed microsomal pellets (containing all of the ribosomes) were suspended in 2 ml of buffer A (S-100 pellet).

To prepare mitochondria, the S10 pellets were suspended in 20 ml buffer A. The suspension was layered on top of a discontinuous Ficoll gradient made up of an equal volume of 12% Ficoll in buffer A (lower layer) and 7.5% Ficoll in buffer A (upper layer). The tubes were centrifuged at 24,000×g for 24 min. The pellets were resuspended in buffer A and centrifuged at 20,000×g for 15 min. The pellets (containing mitochondria) were suspended in 2 ml of buffer A. All fractions were stored at –80° C.

Reductase assay and quantitation of sulindac sulfide formed. With crude cellular fractions when there is a large amount of NADPH oxidation, the NADPH assay described in Example 1 above cannot be used. For use with crude cellular fractions, an extraction assay was developed based on the ability of sulindac sulfide to be extracted into benzene. The reaction mixture for the reduction of sulindac to sulindac sulfide contained in a total volume of 30 µl: 100 mM Tris-Cl, pH 7.4; 0.6 µmoles glucose-6-phosphate; 50 ng glucose-6-phosphate dehydrogenase; 30 nmoles NADPH; 2.5 µg thioredoxin, 1 µg thioredoxin reductase, 50 nmoles sulindac and varying amount of Msr enzymes. Unless stated otherwise, incubations were for 1 hour at 37° C. At the end of the incubation 370 µl of 25 mM Tris-Cl pH 8.0, 100 µl acetonitrile and 1 ml of benzene were added to each tube. After vortexing for 30 seconds and spinning for 1 min at room temperature, the benzene phase was removed and the optical density was read at 350 nm Fifty nmoles of SS or S, when carried through the extraction procedure, gave optical density readings of 0.910 and 0.030, respectively. Under these conditions, virtually all of the SS was extracted into the benzene, while about 2.5% of S was extracted. In some experiments using calf tissue extracts, the standard 30 µl reaction mixture volume was tripled (90 µl) to obtain statistically significant values. The extraction assay was not altered except for reduction of the Tris buffer volume to 310 µl.

To remove the S epimer of sulindac, the sulindac (R, S mixture) was incubated with excess MsrA (4 µg) and DTT for 60 minutes, or until the reaction reached completion. Upon completion, any further reduction seen upon addition of an enzyme fraction in a second incubation would be due to reduction of the R epimer of sulindac.

In some experiments the product was also identified by thin layer chromatography (TLC). After incubation, both the unreacted S and SS product were extracted into 1 ml ethyl acetate. The ethyl acetate phase was removed, dried in a speed vacuum at room temperature and the residue was suspended in 5 µl of ethyl acetate which was then loaded onto a TLC plate. The plate was developed with butanol:acetic acid:water (60:15:25) as the solvent. The compounds were visualized by their yellow color. The Rf values of S and SS were 0.80 and 0.95, respectively.

Results.

Figure 3A:
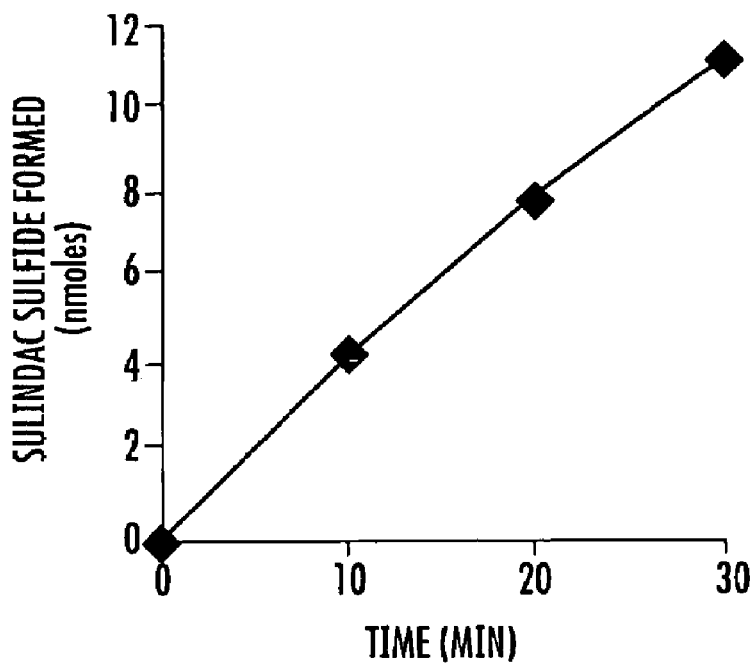
FIGS. 3A and 3B is two graphs showing kinetics of sulindac sulfide production by MsrA, according to an embodiment of the invention.
Figure 3B:
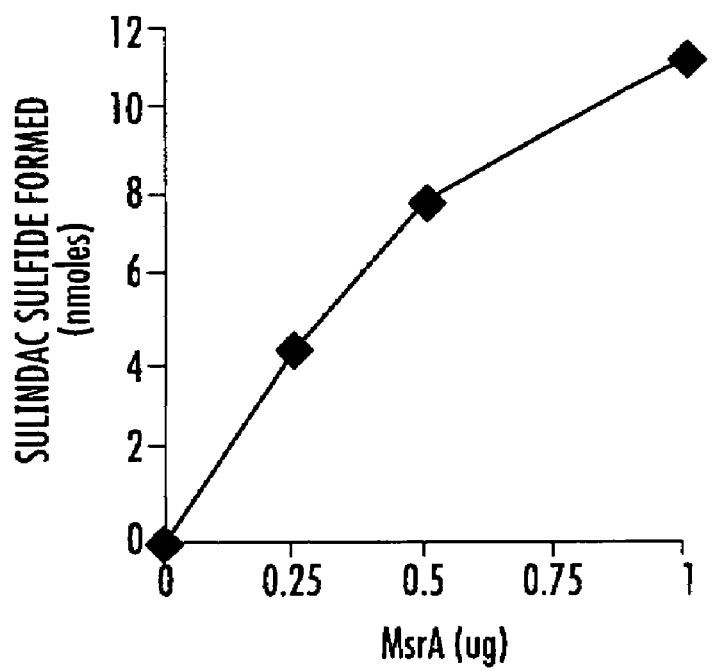

Using the extraction assay described above in Methods, it was found that recombinant MsrA from *E. coli* could reduce S to SS. FIG. 3A shows a time course for the reaction and FIG. 3B shows the effect of MsrA concentration on reduction of S. The reaction was dependent on the thioredoxin reducing system. The product, SS, was independently identified by TLC.

S is a substrate for mem-R, S-Msr. *E. coli* is known to have at least 6 members of the Msr family. Referring to Table 2, these proteins differ in their stereo-specificity, substrate specificity, i.e., free vs. protein-bound Met(O), and location within the cell, i.e., soluble or membrane-associated. Whereas the msrA and msrB genes have been cloned and the recombinant proteins purified, the other soluble *E. coli* Msr enzymes (i.e., fSMsr, fRMsr and MsrA1) have been only partially purified, but have been separated by conventional fractionation procedures using DEAE cellulose chromatography (Etienne, F. et al., Biochem. & Biophys. Res. Comm. 300 (2003) 378-382; Spector, D. et al., Biochem. & Biophys. Res. Comm. 302 (2003) 284-289). The membrane associated Msr (i.e., mem-R, S Msr), which has activity toward both the R and S forms of free and peptide bound met(o), was present as a membrane vesicle preparation.

TABLE 2

Substrate Specificity of Methionine Sulfoxide Reductases in *E. coli*

| ENZYME TYPE | SUBSTRATE | | | |
|---|---|---|---|---|
| | Free-R-(O) | Free-S-(O) | Peptide-R-(O) | Peptide-S-(O) |
| MsrA | | + | | + |
| MsrB | (+) | | + | |
| fRMsr | + | | | |
| fSMsr | | + | | |
| MsrA1 | | | | + |
| Membrane Msr | + | + | + | + |

Brackets ( ) indicate a very weak activity.

Referring to Table 3, S was compared as a substrate for highly purified MsrA and MsrB from *E. Coli* and the partially purified enzyme preparations. The results showed that MsrA and the mem-R,S-Msr are able to reduce S to SS. Very weak activity was observed with MsrA1. S was not a substrate for MsrB, which recognizes peptide-bound Met-S—(O). Table 3. Activity of *E. coli* Msr Enzymes Using Sulindac as a Substrate.

TABLE 3

Activity of *E. coli* Msr Enzymes Using Sulindac as a Substrate.

| ENZYME TYPE | UNITS OF ACTIVITY |
|---|---|
| MsrA | 11.3 |
| MsrB | 0 |
| fRMsr | 0 |
| fSMsr | 0 |
| MsrA1 | <0.9 |
| Membrane | 5.1 |

Unit of activity is defined as nmoles of SS formed per hour. Enzyme concentrations used: 250 ng MsrA; 10 µg MsrB; 290 µg fRMsr; 200 µg fSMsr; 40 µg MsrA1; 50 µg membrane fraction.

Referring now to Table 4, it is seen that the membrane bound Msr of *E. Coli*, which likely contains more than one Msr activity, reduces primarily the R form of sulindac. In these experiments either S, which is a mixture of the R and S epimers, or the R epimer of sulindac (see Methods) were used as substrates. Both exhibited similar activities. Although these results support the R form being reduced, definitive proof may require the chemical synthesis and assay of each epimer of S.

TABLE 4

Membrane Msr of *E. coli* Reduces Primarily the R Epimer of Sulindac.

| SUBSTRATE | NMOLES FORMED |
|---|---|
| Sulindac (R, S) | 2.75 |
| Sulindac (R) | 2.41 |

R epimer of sulindac was obtained by incubating sulindac (R, S) with excess MsrA as described in Methods to remove the S epimer. 35 µg of membrane fraction was used.

Reduction of sulindac in mammalian (bovine) tissues. Results shown in Table 5 reveal that crude homogenates (S-10 fractions, see Methods) of calf liver, kidney and brain are able to reduce S. Of the tissues tested, kidney has the highest specific activity, and brain the lowest.

TABLE 5

Sulindac Reductase Activity in Calf Tissues.

| TISSUE | SPECIFIC ACTIVITY |
|---|---|
| Liver | 4.39 |
| Kidney | 6.53 |
| Brain | 2.31 |

The preparation of the various S-10 fractions are described in Methods. Specific activity is given as nmoles of product formed per hour per mg of protein.

The liver extracts were fractionated and mitochondria, S-100 and S-100 pellet (microsomes) were prepared as described in Methods. As shown in Table 6, all three cellular fractions were able to reduce S to SS. The identity of the enzyme(s) responsible for the activity was not determined, but preliminary evidence indicated that MsrA was largely responsible, based on the observation that the addition of excess amounts of Met-S—(O) inhibited the activity in all three fractions, whereas the addition of Met-R—(O) had only a slight effect. Thus the responsible enzyme had Met-S—(O) activity. Because free Met(O) Msr enzymes (i.e., FSMsr and FRMsr) cannot reduce sulindac (Table 2), MsrA is most likely the enzyme responsible for this activity.

TABLE 6

Subcellular Distribution Sulindac Reductase
Activity in Bovine Liver.

| LIVER FRACTIONS | SPECIFIC ACTIVITY |
|---|---|
| S-10 | 4.39 |
| S-100 | 6.20 |
| Mitochondria | 2.44 |
| Microsomes | 1.31 |

The indicated liver fractions were prepared as described in Methods. Specific activity is given as nmoles of product synthesized per hour per mg of protein.

Example 3

Synthesis of Sulindac Methionine Catalytic Antioxidants

As shown above, sulindac is a substrate for MsrA but not for MsrB. Sulindac contains a methyl sulfoxide moiety which is recognized by MsrA enzymes, but does not contain a N-methionine sulfoxide moiety (see FIG. 2), the substrate recognized by both MsrA and MsrB enzymes (Table 2). This example describes schemes for the chemical synthesis of derivatives of sulindac that are improved as substrates for multiple Msr enzymes including MsrB, by modification to contain an N-substituted methionine, in which the methionine amino group is in peptide or amide linkage.

Figure 4A:
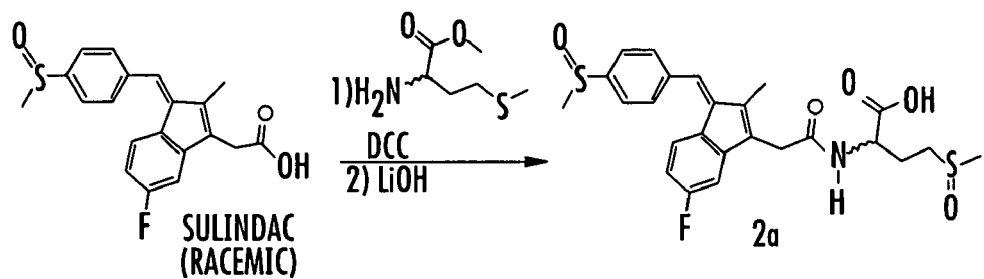
FIGS. 4A and 4B is a schematic diagram showing chemical synthetic pathways for making methionine derivatives of sulindac (compounds 2a and 3a), according to an embodiment of the invention.
Figure 8:
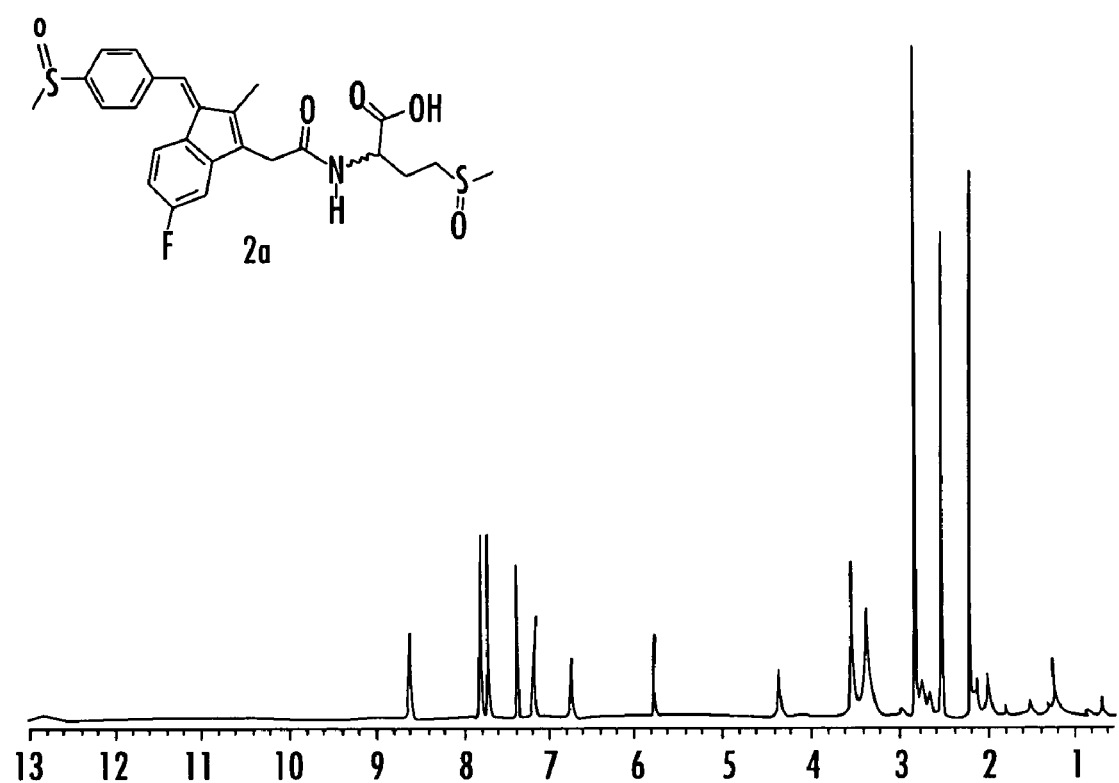
FIG. 8 shows a NMR spectrum of compound 2a of the invention.

Referring to FIG. 4A, compound 2a (1(Z)-5-fluoro-2-methyl-1-[4-(methylsulfinyl)phenyl]methylene]-1H-indene-3-[1-methylthiomethylenyl-2-aminoacetyl]propanoic acid) is shown. Compound 2a contains a methionine group linked through the amino group to the acetyl moiety of sulindac. This compound was synthesized starting from sulindac and methionine sulfoxide methyl esters as follows. To a 50 ml round bottom flask under an argon atmosphere fitted with a teflon stir bar and rubber stopper, 1.4 mmol of sulindac was dissolved in 20 ml DMF followed by the addition of 1.5 mol of methionine sulfoxide methyl ester. Dicyclohexylcarbodiimide (1.2 mmol), triethylamine (2.0 mmol) and 4-dimethylaminopyridine (0.05 mmol) were placed in the reaction flask. After 12 hours, TLC analysis (75% ethyl acetate in hexanes) showed the formation of the product at $R_f=0.29$. The reaction mixture was then placed onto a 2.5 cm diameter flash column filled with approximately 6 inches of silica gel and topped off with a quartz sand plug. The following elution sequence was used: 5% EtOAc/Hex (250 mL), 30% EtOAc/Hex (500 mL), 50% EtOAc/Hex (250 mL) and a final elution of 85% EtOAc/Hex (250 mL). HPLC analysis of the compound (gradient elution from 5% to 95% MeCN/$H_2O$ over 45 min) gave a peak at 22.5 min with 98% purity. Proton NMR analysis of compound 2a is shown in FIG. 8.

Figure 4B:
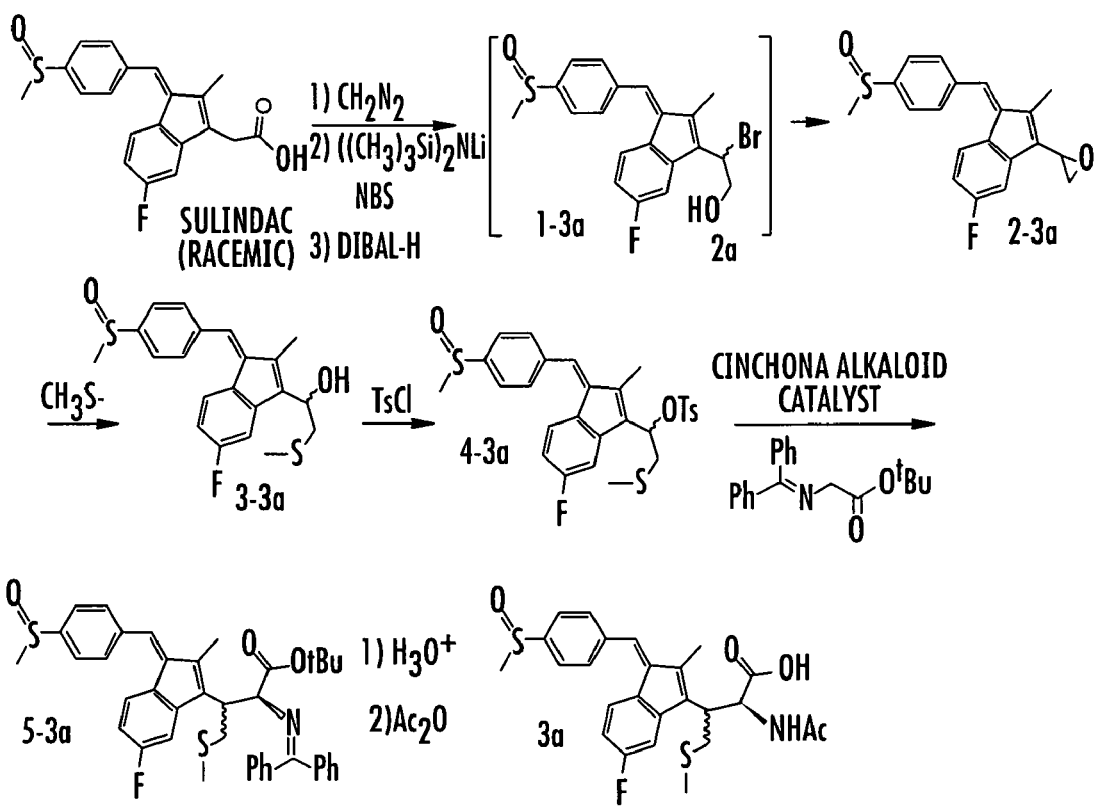

Another methionine derivative of sulindac, i.e., compound 3a, is given in FIG. 4B. A suitable scheme for the synthesis of compound 3a, with control of the α-carbon stereochemistry, is shown. In this particular synthetic method, the synthesis begins with commercially available sulindac (racemic form). The sulindac is converted to its methyl ester by treatment with diazomethane ($CH_2N_2$). The methyl ester is then treated with a strong base to form the enolate, followed by quenching with N-bromosuccinimide (NBS) leading to the α-bromoester (Kita et al., J. Am. Chem. Soc. 123:3214, 2001). The ester group of this intermediate is then selectively reduced to the primary alcohol using diisobutylaluminum hydride (DIBAL-H), according to the method of Fukuyama et al., J. Am. Chem. Soc. 116:3125, 1994, to give intermediate compound 1-3a. Compound 1-3a epoxidizes to give intermediate compound 2-3a. Treatment of compound 2-3a with methyl sulfide is expected to lead to the β-hydroxysulfide compound 3-3a (Conte et al., Tetrahedron Lett. 30:4859, 1989). Using para-toluene sulfonylchloride (TsCl), the hydroxyl group in compound 3-3a is converted to the corresponding tosylate (compound 4-3a). By an extension of the method of O'Donnell (O'Donnell et al., J. Am. Chem. Soc. 111:2353, 1989), the tosylate on compound 4-3a reacts with a protected diphenylimino-glycine derivative under the influence of a cinchona alkaloid asymmetric phase-transfer catalyst. This reaction gives the corresponding α-imino ester (compound 5-3a), with control over the stereochemistry of the α-carbon. Subsequent aqueous hydrolysis of the imino and tert-butyl ester groups gives the desired compound 3a.

Figure 5A:
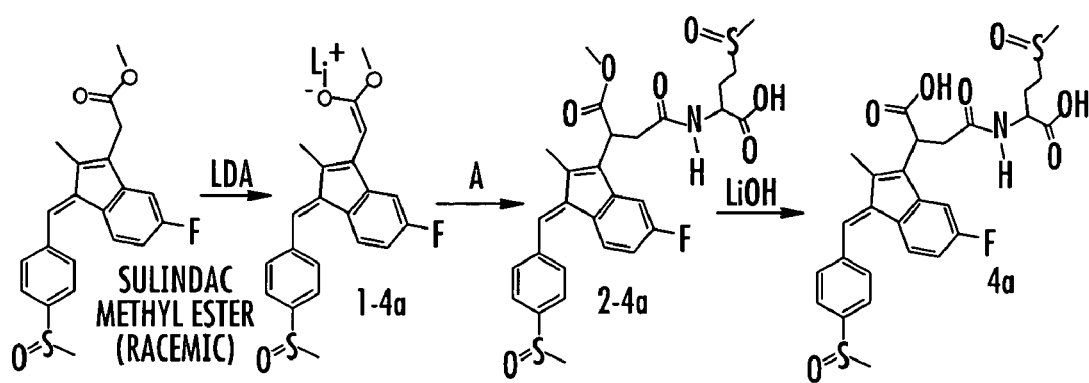
FIGS. 5A and 5B is a schematic diagram showing chemical synthetic pathways for making methionine derivatives of sulindac (compounds 4a and 5a), according to an embodiment of the invention.

Referring now to FIG. 5A, sulindac contains a methylene group adjacent to a carboxyl that is easily converted into enolate 1-4a. Lithium diisopropylamide (LDA) is a base typically used to form these types of enolates. Intermediate 1-4a should react with bromoacetyl methionine sulfoxide (A) to form the new carbon-carbon bond found in 2-4a. Hydrolysis of this intermediate with lithium hydroxide gives the corresponding carboxylic acid derivative (compound 4a).

Figure 5B:
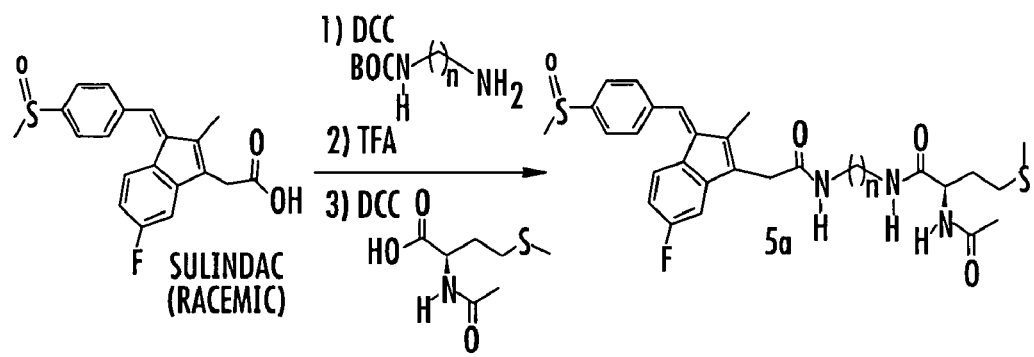

FIG. 5B illustrates yet another embodiment of an N-methionine derivative of sulindac indicated as compound 5a. In compound 5a, the sulindac structure and the N-acetyl methionine group are tethered by a diamine chain that can be of varying length. The use of such a linker molecule provides the ability to generate a large variety of methionine derivatives through combinatorial synthesis methods. Compound 5a may be obtained as follows (FIG. 5B). Under the action of DCC, sulindac is coupled to tert-butoxycarbonyl (BOC) mono-protected diamine, followed by removal of the BOC protecting group under acidic conditions using trifluoroacetic acid (TFA). This intermediate is coupled to N-acetyl methionine in the presence of DCC to give compound 5a. Compound 5a can easily be obtained as the single enantiomer (or epimers of the sulfoxide position). The addition of N-acetyl methionine moieties is preferred, as these moieties are expected to act as a substrate for enzymes that recognize N-blocked methionine sulfoxide, (such as MsrA and MsrB). D amino acids may be preferred to minimize metabolism. A racemic mixture of the sulfoxides (i.e., both R and S forms) is preferred if it is desired to have the compound function as a substrate for most, if not all, known Msr family enzymes that recognize free or protein-bound forms of methionine sulfoxide (whether R or S epimers).

Example 4

Synthesis of Methionine Catalytic Anitioxidants Derived From Salicylic Acid and Mefenlanic Acid This example describes chemical synthetic schemes suitable for preparing bi-functional compounds that can serve both as catalytic antioxidants and anti-inflammatory agents (COX inhibitors).

As described above, sulindac is one example of a COX inhibitor. This example describes methionine derivatives of other COX inhibitors, i.e., acetyl salicylic acid and mefenamic acid. These bifunctional antioxidant compounds contain the amino group of methionine in the form of an amide and preferably retain the carboxyl group found in the parent compounds that may be critical to their inhibitory action.

Figure 6A:
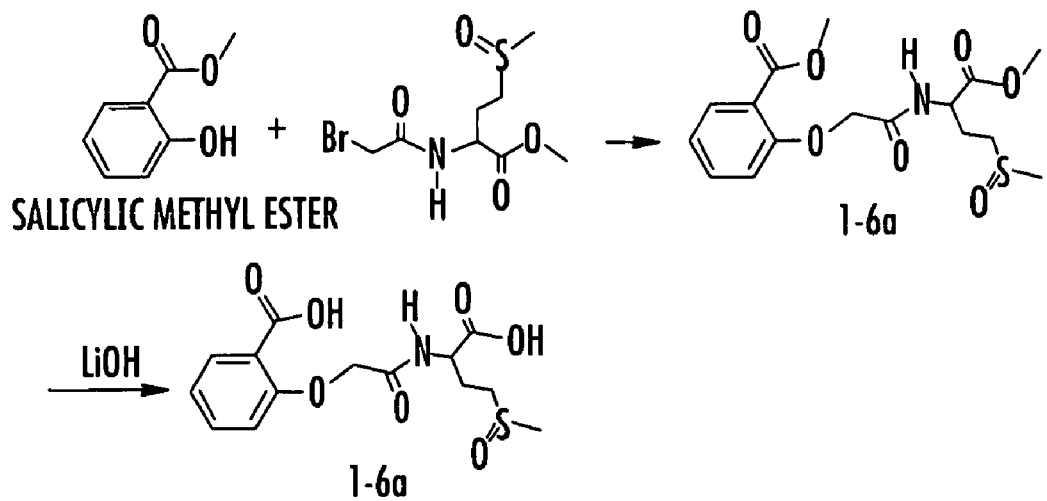
FIGS. 6A and 6B is a schematic diagram showing chemical synthetic pathways for making catalytic antioxidants based on salicylic acid and mefenamic acid (compounds 6a and 7a, respectively), according to an embodiment of the invention.
Figure 6B:
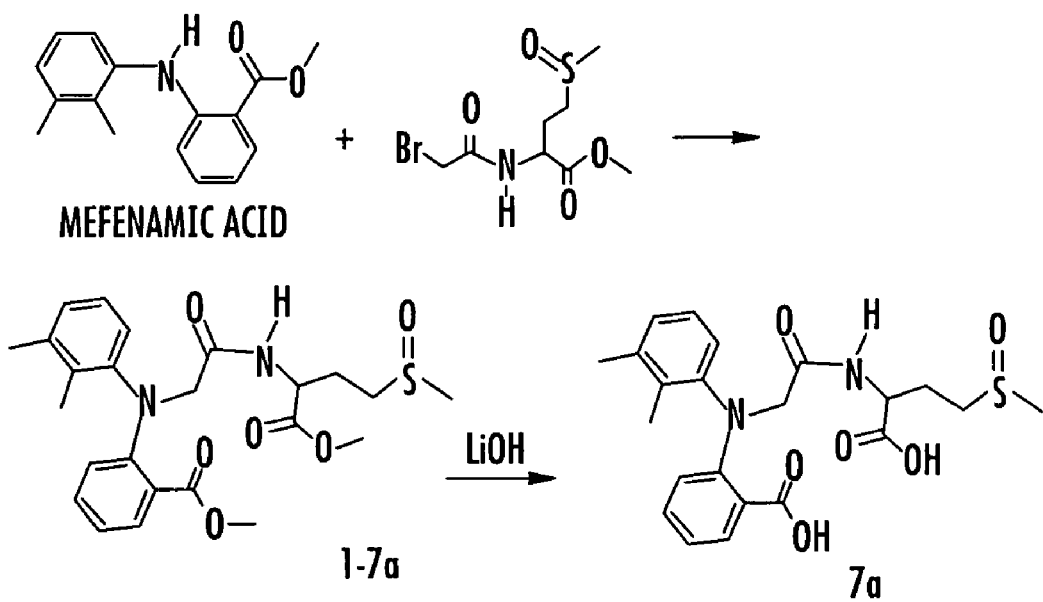

Referring to FIG. 6A, starting from the methyl ester of salicylic acid, the phenol hydroxy group is shown to react with the carbon bearing the bromine in bromoacetylmethionine sulfoxide (BAMS) to form the oxygen-carbon bond of intermediate 1-6a. In the case of mefenamic acid, the reaction with BAMS is shown to occur at the amine nitrogen to give intermediate 1-7a (FIG. 6B). The salicyclic and mefenamic methionine sulfoxide derivatives can be converted to the respective carboxylic acid products 6a and 7a using a mild hydrolysis reaction with lithium hydroxide (LiOH).

Example 5

Synthesis of Methionine Catalytic Antioxidants Derived From Ibuprofen, Indomethacin and Rofecoxib/Vioxx®

Figure 7A:
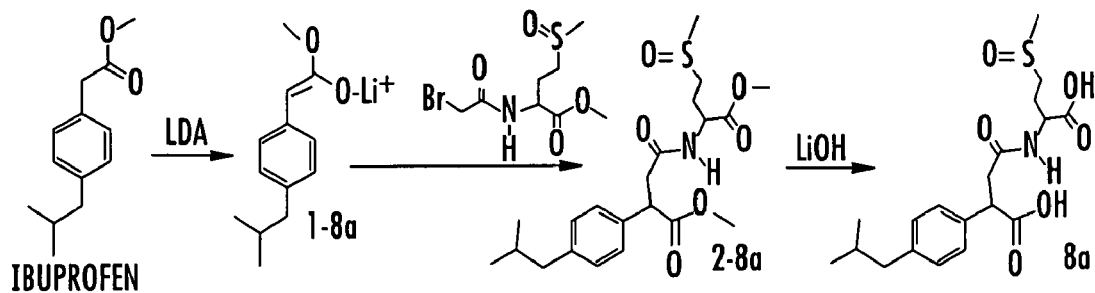
FIG. 7A-C is a schematic diagram showing chemical synthetic pathways for making catalytic antioxidants based on ibuprofen, indomethacin and Vioxx® (compounds 8a, 9a, and 10a, respectively), according to an embodiment of the invention.
Figure 7B:
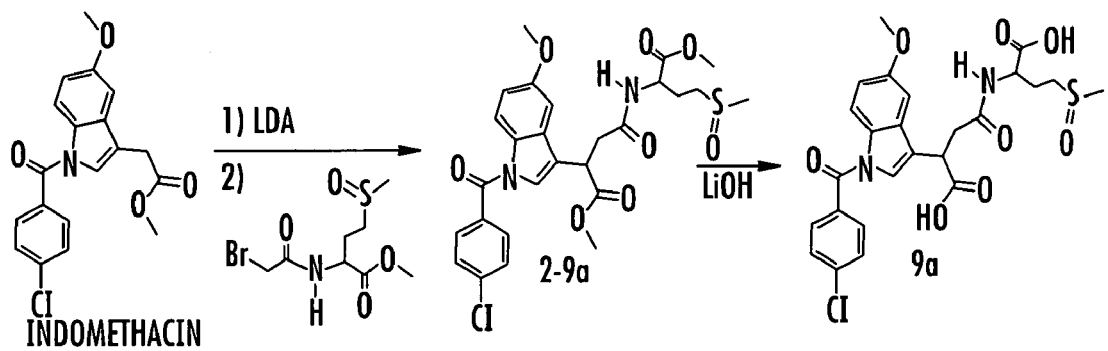
Figure 7C:
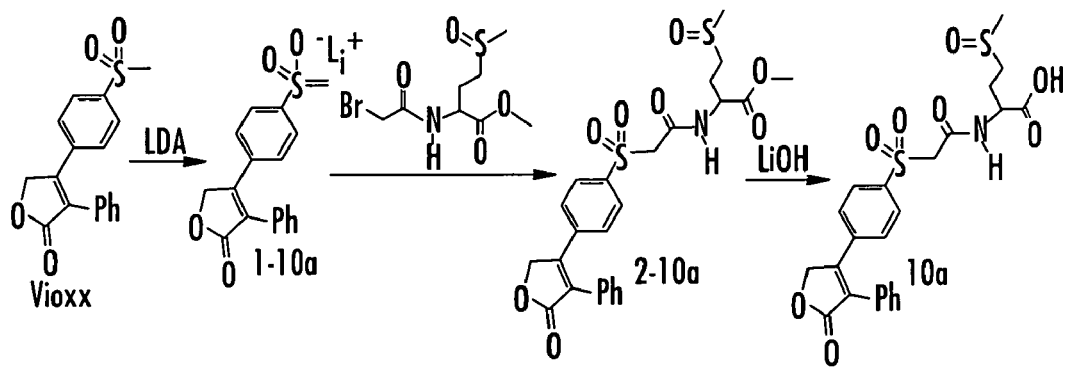

Referring now to FIG. 7, ibuprofen (FIG. 7A), indomethacin (FIG. 7B), and rofecoxib/Vioxx® (FIG. 7C) each contain a methylene group adjacent to a carboxyl or a sulfonyl group that is easily converted into enolate, shown for intermediates 1-8a and 1-10a. Lithium diisopropylamide (LDA) is a typical base used to form enolates. Intermediates 1-8a, 1-9a, and 1-10a are shown to react with bromoacetyl methionine sulfoxide to form the new carbon-carbon bonds in intermediates 2-8a, 2-9a, and 2-10a. Hydrolysis of these intermediates with lithium hydroxide gives the corresponding carboxylic acid derivatives (compounds 8a, 9a, and 10a).

Example 6

Sulindac Methionine Sulfoxide is a Substrate for MsrA and MsrB

As shown above, sulindac is a substrate for MsrA but not for MsrB. Referring to FIG. 4A, unmodified sulindac contains a methyl sulfoxide moiety, but does not include within its structure a methionine sulfoxide moiety, the required substrate for Msr B enzymes. Sulindac methionine sulfoxide (SMO), an N-acetyl methionine sulfoxide derivative of sulindac described in Example 4 above includes both a methyl sulfoxide and a methionine sulfoxide (see, for instance, compound 2a in FIG. 4A). This example demonstrates that SMO can serve as a substrate for both MsrA and MsrB enzymes.

Materials and Methods.

Synthesis of SMO. Sulindac methionine sulfoxide (SMO) was synthesized according to the synthetic pathway described in Example 3 supra. Compound 2a was used for these experiments.

Reductase assay and thin layer chromatography (TLC). Reaction mixtures were prepared in duplicate for assay of the reduction of sulindac (S) and sulindac methionine sulfoxide (SMO). Mixtures contained in a total volume of 30 μl: 100 mM Tris-Cl pH 7.4, 15 mM DTT, 100 nmoles of S or SMO, 3 μg of MsrA enzyme, or 21 μg of MsrB enzyme. Incubation was carried out for 2 hours at 37° C., at the end of which the duplicate samples were combined and dried in a speed-vacuum unit at room temperature. The residue was suspended in 50 μl of ethanol, which was then loaded onto a silica gel TLC plate. The plate was developed with butanol: acetic acid:water (60:15:25) as the solvent. The compounds were visualized by their yellow color.

Results:

As discussed above, it is known that MsrA can reduce methyl sulfoxide moieties that occur as functional groups within free and peptide-bound methionine (i.e., Met(O)), but also within other molecules. By contrast, MsrB can only reduce Met(O), and works best with Met(O) in peptide linkage (see Table 2). Accordingly, based on the known substrate specificity of MsrA and MsrB, several different products would be predicted upon reaction of sulindac and SMO with MsrA and MsrB. For example, because the structure of sulindac (S) contains only a methyl sulfoxide (as seen in FIG. 2), reduction of S by MsrA results in SS. Reduction of S by MsrB would not be expected to generate a product, due to the absence of methionine sulfoxide in S. In contrast to unmodified S, SMO includes both the methyl sulfoxide group of S as well as the methyl sulfoxide included in the methionine group (see, for example, compound 2a in FIG. 4A). Accordingly, reaction of SMO with MsrA could generate several possible products having one or the other, or both methyl sulfoxide groups reduced, i.e.: sulindac sulfide methionine sulfoxide (SSMO), sulindac methionine (SM), or sulindac sulfide methionine (SSM). With MsrB, however, only the methionine sulfoxide should be reduced and the expected product is SM.

Figure 9:
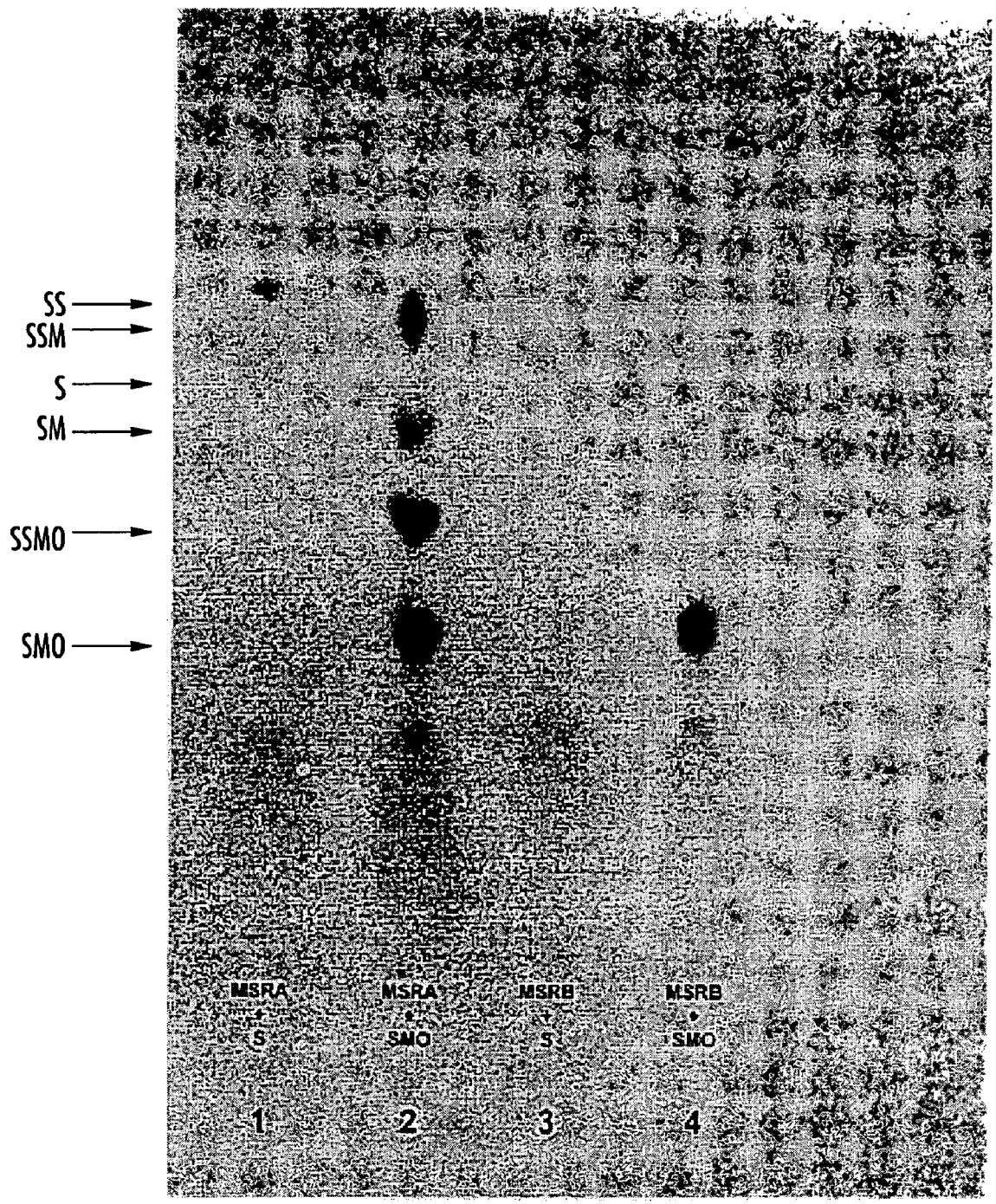
FIG. 9 is a micrograph of a TLC plate showing the presence of reduction products of sulindac (S) and sulindac methionine sulfoxide (SMO) following incubation with MsrA and MsrB enzymes. Results demonstrate that S is a substrate for MsrA and that SMO is a substrate for both MsrA and MsrB.

FIG. 9 shows TLC results from the various incubations, i.e., MsrA+S (lane 1); MsrA+SMO (lane 2); MsrB+S (lane 3) and MsrB+SMO (lane 4). In FIG. 9, the indicated substrates and reaction products are as follows: S—sulindac; SS—sulindac sulfide; SM—sulindac methionine; SSM—sulindac sulfide methionine; SMO—sulindac methionine sulfoxide; SSMO—sulindac sulfide methionine sulfoxide. The positions where the substrates, products and standards migrate on the TLC plate are indicated by arrows.

The results of the enzyme assays demonstrate the following. Lane 1 shows the presence of SS, indicating that sulindac is a substrate for MsrA. Lane 2 reveals formation of SSM, SM, and SSMO, demonstrating that SMO is a substrate for MsrA and that both methly sulfoxide groups can be reduced. Lane 3 shows only S, demonstrating that unmodified sulindac is not a substrate for MsrB. By contrast, lane 4 reveals that SMO is a substrate for MsrB, shown by the formation of SM (FIG. 9) Thus it is shown that a methionine derivative of sulindac, i.e., SMO, can act as a substrate for both MsrA and MsrB enzymes.

Example 7

Sulindac Increases Resistance to Oxidative Stress in *Drosophila*

This example demonstrates that sulindac, an antioxidant containing a methyl sulfoxide moiety, can extend the lifespan of flies subjected to an agent known to kill flies via production of ROS.

Materials and Methods.

Paraquat is a cytotoxic compound known to form superoxide radicals intracellularly. Three different concentrations of paraquat (i.e., 2.5 mM, 5 mM and 10 mM) were tested. Flies (*Drosophila*) were raised for 3 days on apple juice medium (33% apple juice, 1.7% sucrose and 2.7 mg/ml methyl paraben, a mold inhibitor, in 3.5% agar) containing various concentrations of sulindac or no supplement (Controls). After 3 days at 25° C., flies were transferred to test vials for counting.

Results.

Figure 10:
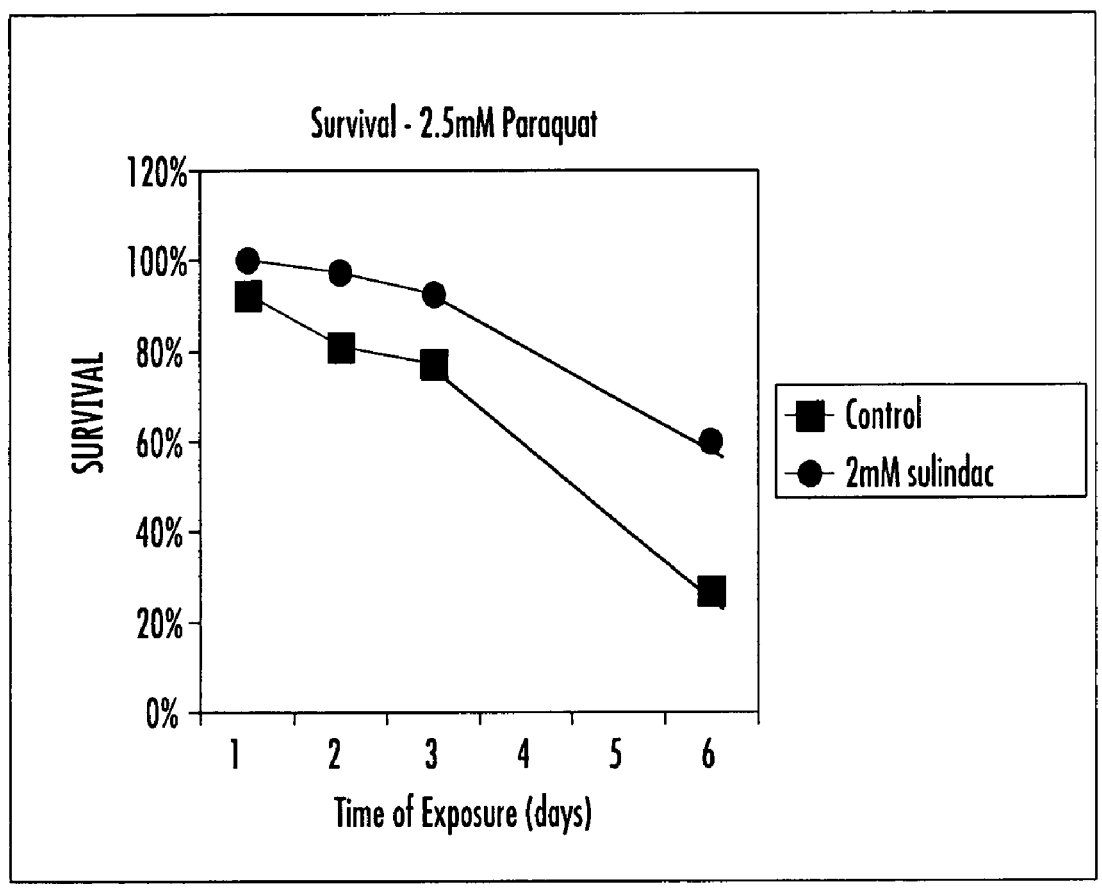
FIG. 10 is a graph showing enhanced survival of sulindac-treated flies exposed to oxidative stress induced by paraquat.

In the group treated with 2.5 mM paraquat, approximately 80% and 25% of the flies in the untreated control group, respectively, were alive after 3 and 6 days of paraquat exposure. By contrast, approximately 95% and 60%, respectively, of the flies treated with 2 mM sulindac remained alive at the 3 day and 6 day time points (FIG. 10). Similar results were observed in the groups exposed to higher concentrations of paraquat. For example, in groups exposed to 10 mM paraquat, the respective survival rates after 2 and 3 days were approximately 50% and 17% in the controls and 85% and 57% in the sulindac treated groups. These results demonstrate that administration of a methyl sulfoxide-containing compound that is a substrate for MsrA can lengthen the lifespan of paraquat-exposed flies. Earlier studies showed that over expressing MsrA enzyme in transgenic flies extended their lifespan. The present data provide evidence that increasing the intracellular level of a substrate for the Msr system can also provide a protective effect against damaging ROS species, leading to increased longevity under conditions of oxidative stress.

Example 8

Sulindac Promotes Cell Survival in Neuronal Cells Subjected to Oxidative Damage by MPP+

This example demonstrates a protective effect of sulindac on PC-12 cells following insult with MPP+, a toxic compound that selectively destroys dopaminergic neurons in vitro, and in an in vivo animal model of Parkinson's disease.

Materials and Methods.

MPP+ neurotoxin. The neurotoxin 1-methyl-4 phenyl-1,2,3,6-tetrahydropyridine (MPTP) when given to both humans and primates results in a clinical syndrome closely similar to Parkinson's disease. The compound is metabolized to 1-methyl-4-phenylpyridinium (MPP+) by monamine oxidase B and is subsequently selectively taken up by dopaminergic terminals and concentrated in the neuronal mitochondria in the substantia nigra. MPP+ inhibits complex 1 of the electron transport chain and is thought to cause irreversible inactivation of the complex by generating free radicals (Hartley A., Stone J. M., Heron C, Cooper J. M., and Schapira A. H. V. J. Neurosci. 63:1987-1990, 1994) MPP+ increases superoxide synthesis in vivo and in vitro. MPP+ damage is decreased in transgenic mice overexpressing superoxide dismutase, suggesting that free radicals are involved in its neurotoxicity.

Cell culture. PC-12 cells were initially grown overnight in Dulbecco's modified Eagle's medium containing high glucose (Gibco # 11195-065), 5% fetal calf serum and 10% horse serum in 9 cm dishes. The cells were then transferred to 6 cm dishes and grown in the same medium without glucose but using sodium pyruvate (Gibco # 11966-025) as the sole energy source These cells were pretreated with sulindac (Sigma) at concentrations of 0.1, 0.2, or 0.5 mM for 48 hours, the medium containing the sulindac was removed and replaced with fresh medium The cells were then incubated for 24 hours in medium containing MPP+ at a final concentrations of 0.2 mM. Control cells were incubated in MPP+-free medium. At the end of the 24 hr period, cell viability was assayed by trypan blue exclusion.

Results.

Referring to Table 7, the results show that 0.2 mM MPP+ was highly toxic to PC-12 cells, causing approximately 85% of the cells to die (15% cell survival) following a 24 hour treatment with this compound. Pretreatment with sulindac prior to MPP+ insult was protective against cell death, exhibiting a dose-response with approximately 35% cell death (65% cell survival) following pretreatment with the maximum concentration tested, i.e., 0.5 mM. In the absence of MPP+, sulindac had no effect on the viability of the cells.

TABLE 7

Effect of Sulindac on the Viability of PC-12 Cells Treated with MPP+.

| Sulindac (mM) | Dead cells (%) Exp 1 | Dead cells (%) Exp 2 |
| --- | --- | --- |
| 0 | 85 | 87 |
| 0.1 | 67 | 74 |
| 0.2 | 55 | 39 |
| 0.5 | 34 | 35 |

Example 9

Sulindac Extends the Lifespan of a Transgenic Mouse Model of Familial Amyotrophic Lateral Sclerosis (ALS)

This example provides evidence that sulindac, a methyl sulfoxide containing compound that acts as a substrate for MsrA enzymes can significantly extend lifespan, increase motor neuron cell count and improve motor performance in a mouse model of ALS based on a mutation in superoxide dismutase (SOD1).

Materials and Methods:

ALS is an adult onset neurodegenerative disease of generally unknown etiology. ALS is most commonly sporadic, with about 10% of cases being inherited as an autosomal dominant familial form. It is now known that about 20% of the familial cases are associated with a mutant form of Cu/Zn SOD (Rosen, D. R., et. al., (1993) Nature 362:59-62 ). Although the protein harbors a mutation (over 100 different SOD mutations having been documented in ALS patients), it is still enzymatically active. Oxidative damage is one of the main hypotheses for the toxicity of the mutant protein. The animals used in this study express a mutant form of SOD that models a mutation described in patients with ALS.

Transgenic mice expressing a mutant form of SOD similar to that found in human ALS patients were used for this study. Transgenic male mice with a G93A human SOD1 (GIH/+) mutation (B6SJL-TgN (SOD1-G93A)1 Gur; Jackson Laboratories, ME) were used to breed with female B6SJL mice (Jackson Laboratories, Me.). The F1 generations were genotyped for the G93A mutation with polymerase chain reaction (PCR) using tail DNA, and two specific primers from the SOD1 gene.

Sulindac administration. G93A mice were treated with sulindac at two different doses, i.e., 300 PPM and 450 PPM, which was mixed into their food beginning on postnatal day 30. Three groups were examined (i.e., 300 PPM, 450 PPM sulindac and controls). Motor performance was assessed by Rotarod testing for each group and survival time was recorded.

Motor function testing. Mice were trained for 2-3 days to become acquainted with the Rotarod apparatus (Columbus instruments, Columbus, Ohio). Rotarod performnances were assessed in G93A mice starting at 60 days of age. The testing began with placing the mice on a rod that rotates at 12 rpms. The time period that the mice stayed on the rod before falling off was recorded as a measurement of the competence of their motor function. Three trials were performed, and the best result of the three trials was recorded representing the status of the motor performance. Mice were tested twice a week until they could no longer perform the task.

Survival times. The initial sign of disease in G93A transgenic mice is a resting tremor that progresses to gait impairment, asymmetrical or symmetrical paralysis of the hind limbs, and ultimately complete paralysis at the end stage. Mice were sacrificed when they were unable to roll over within 20 seconds after being pushed on their side. This time point was determined to be the time of survival, at which time the mice were sacrificed.

Light microscopic immunocytochemistry. Mice were perfused transcardially with cold 0.1 M phosphate-buffered saline (PBS) for 1 minute followed by cold 4% paraformaldehyde in PBS for 10 minutes. The spinal cords were removed rapidly, blocked coronally, and post-fixed in 4% paraformaldehyde in PBS for 6 hours. Blocks were cryoprotected in 30% sucrose for 24 hours and were sectioned on a cryostat at a thickness of 35 micrometers. All protocols were conducted within NIH guidelines for animal research and were approved by the Institutional Animal Care and Use Committee (IACUC).

Serial transverse sections (50 μm thick) were cut on a cryostat and collected for Nissl staining. Every fourth section was analyzed for neuronal volume and number using the optical fractionator and nucleator probes of the Stereo Investigator System (Microbrightfield, Colchester, Vt.). Six tissue sections of the lumbar spinal cord from each mouse were analyzed. All cells were counted from within the ventral horn below a horizontal line across the gray matter through the ventral border of the central canal. Photomicrographs were taken on a Zeiss Axiophot II microscope.

Statistical analysis. Statistical analysis of survival was performed using Kaplan-Meier test for survival measured in postnatal days, Fisher's Test for mean age of death analysis, and Scheffe test for motor performance.

Figure 11:
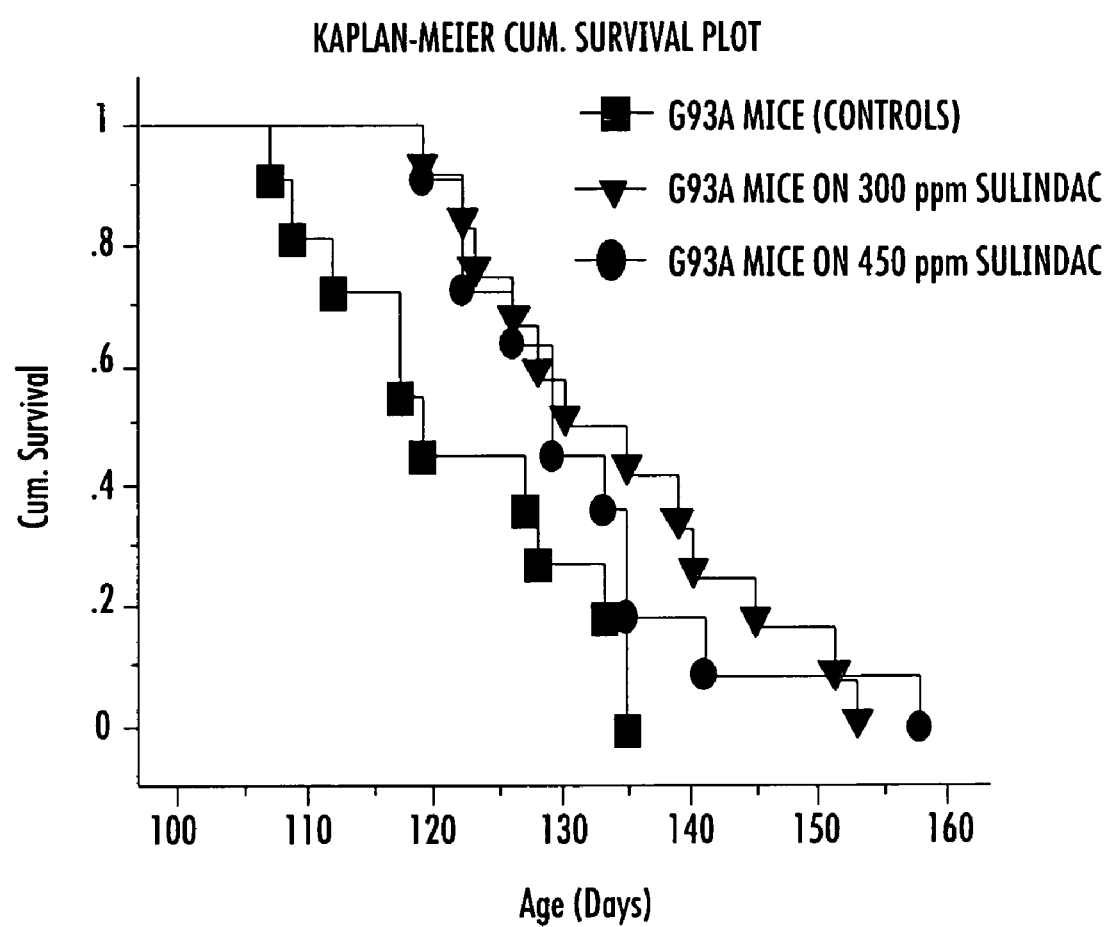
FIG. 11 is a graph showing enhanced survival of G93A transgenic mice over expressing a mutant superoxide dismutase with neurodegenerative disease treated with sulindac.

Results:

Referring to FIG. 11, G93A mice treated with 450 PPM sulindac survived an average of 131.17±10.9 days. This was a 7% increase over control mice, which survived an average of 123.16±11 days (P=0.083). G93A mice treated with 300 PPM sulindac also exhibited extended survival (a 10% increase) relative to the controls, with mean survival time of 135.17±11.4 days (P=0.02).

The results of several statistical tests of the data shown in FIG. 11 are presented in Table 8.

TABLE 8

Rank Test

|  | Chi-Square | DF | P-Value |
|---|---|---|---|
| Logrank (Mantel-Cox) | 6.744 | 2 | .0343 |
| Breslow-Gehan-Wilcoxon | 7.796 | 2 | .0203 |
| Tarone-Ware | 7.374 | 2 | .0250 |
| Peto-Peto-Wilcoxon | 7.661 | 2 | .0217 |
| Harrington-Fleming (rho = .5) | 7.374 | 2 | .0250 |

Figure 12:
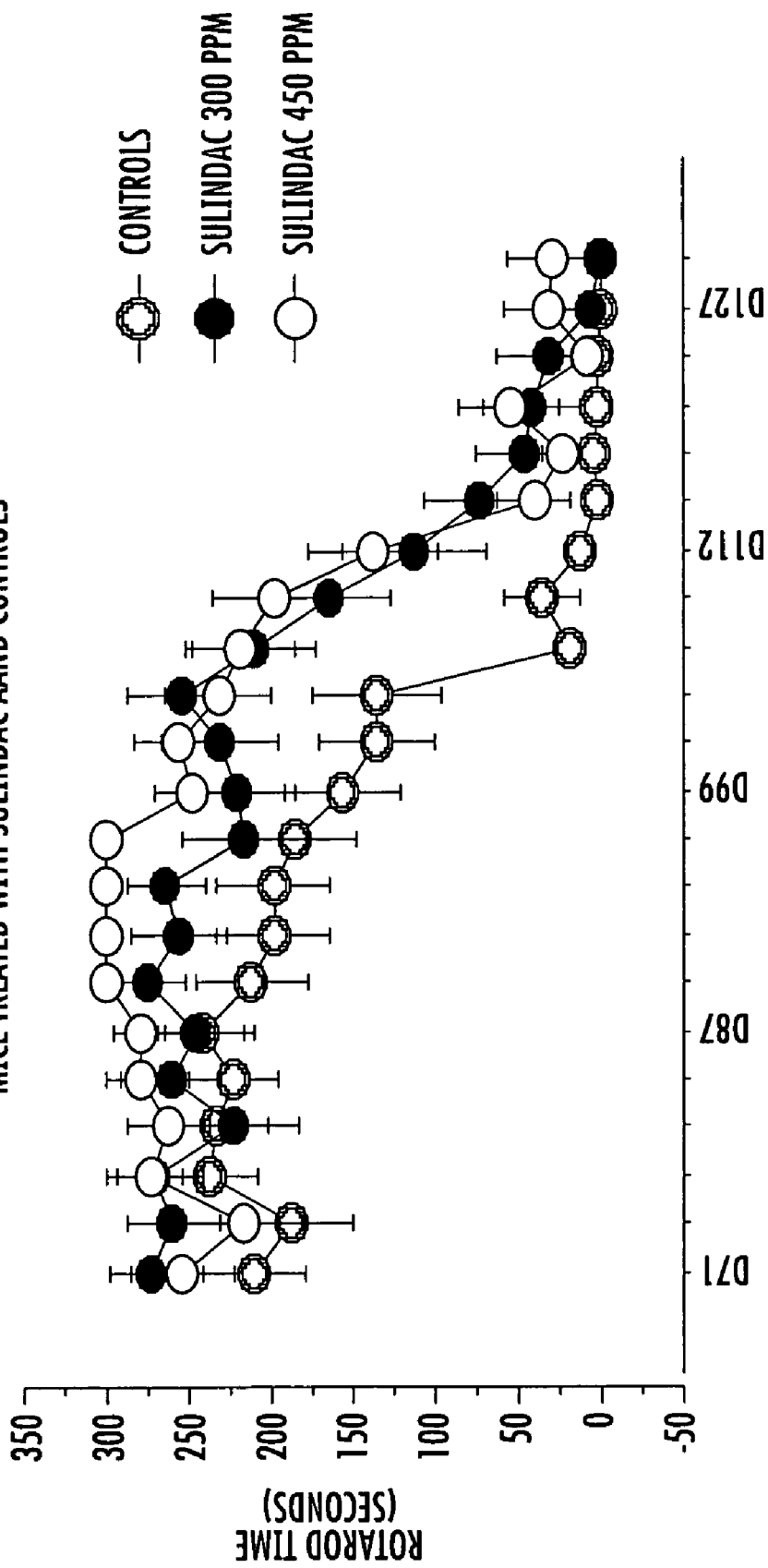
FIG. 12 is a graph showing enhanced motor performance of sulindac-treated transgenic G93A mice.
Figure 13:
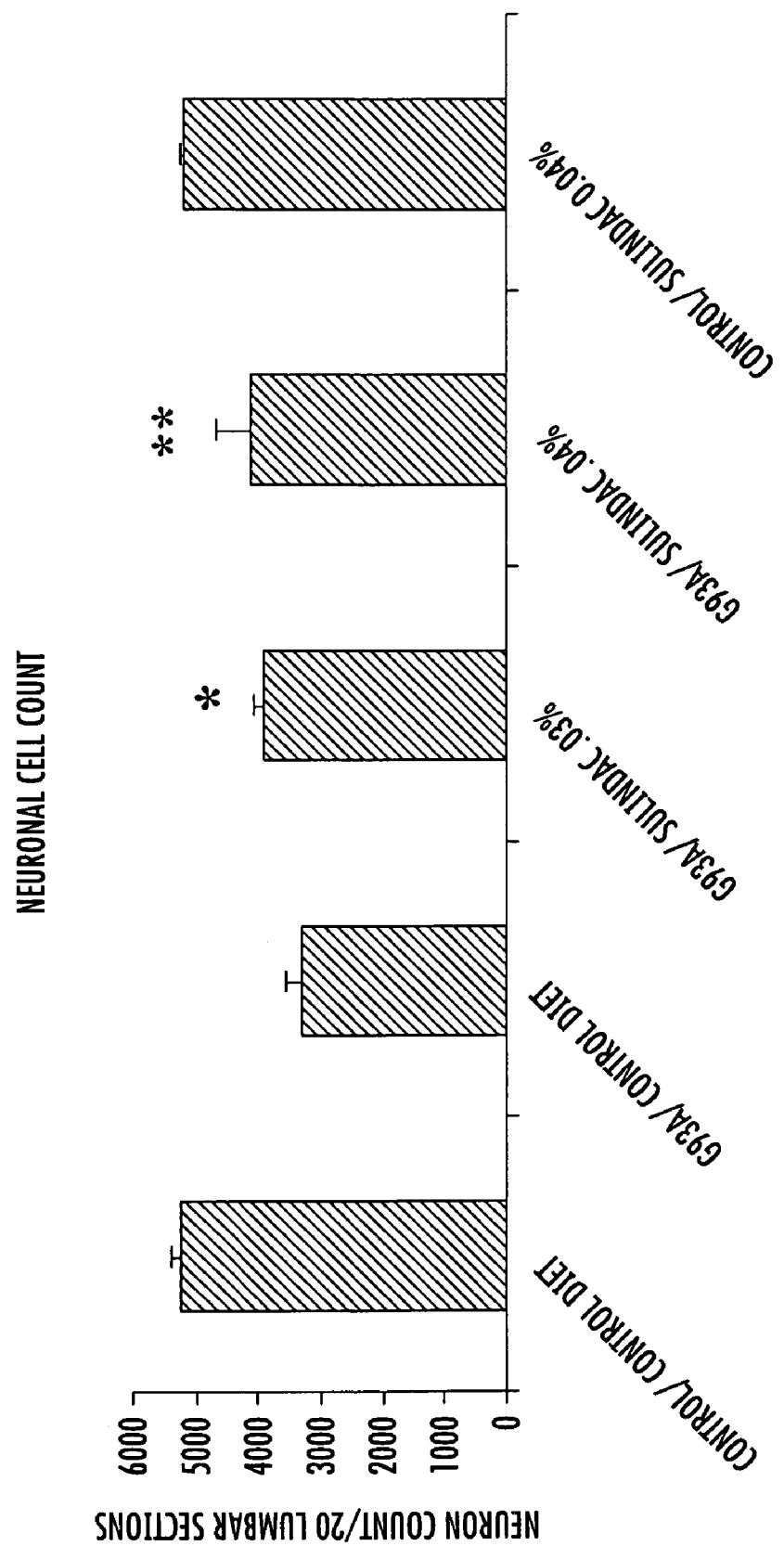
FIG. 13 is a graph showing neuronal cell counts in sections of spinal cords of G93A mice. Neuronal cell survival is significantly higher in animals receiving sulindac.

The sulindac-treated groups showed a significant improvement in motor performance, as evaluated by Rotarod performance times (FIG. 12). Microscopic analysis of spinal cord sections revealed that the sulindac-treated mice had significantly higher counts of motor neurons as compared with G93A controls (FIG. 13): Differences between the 300 PPM and 450 PPM sulindac groups were not significant (FIG. 13 and Table 9).

TABLE 9

Scheffe for Motor Performance

|  | Mean Diff. | Crit. Diff. | P-Value |  |
|---|---|---|---|---|
| Controls, Sulindac 300 PPM | −59.443 | 54.695 | .0308 | S |
| Controls, Sulindac 450 PPM | −73.119 | 53.271 | .0053 | S |
| Sulindac 300 PPM, Sulindac 450 PPM | −13.676 | 56.815 | .8267 |  |

OTHER EMBODIMENTS

This description has been by way of example of how the compositions and methods of the invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A non-naturally occurring compound comprising at least one methyl sulfoxide moiety, or a pharmaceutically acceptable salt thereof, the compound having formula 6 or a pharmaceutically acceptable salt thereof:

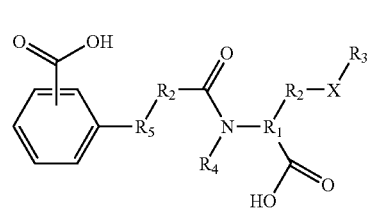

6 wherein:
the aromatic ring is a 6-membered heteroaromatic ring; the aromatic carboxyl group is oriented ortho, meta, or para to the methionine-based moiety; $R_1$ is CH of either R or S configuration; $R_2$ is a normal or branched alkyl or fluoroalkyl group having 1 to 6 carbons; $R_3$ is methyl; $R_4$ is a hydrogen or a normal or branched alkyl group having 1 to 6 carbons; $R_5$ is an oxygen; and X is sulfoxide.

2. The non-naturally occurring compound of claim 1, comprising at least one methyl sulfoxide moiety, said compound having a backbone not based on sulindac (1(Z)-5-fluoro-2-methyl-1[[4-(methylsulfinyl)phenyl)methylene]-1H-indenyl-3-acetic acid).

3. A non-naturally occurring compound comprising at least one methyl sulfoxide moiety, or a pharmaceutically acceptable salt thereof, said compound having formula 7 or a pharmaceutically acceptable salt thereof:

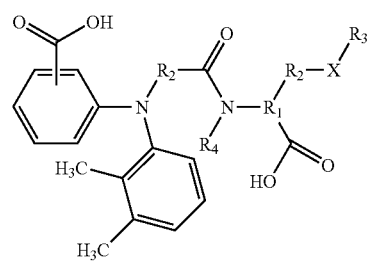

7 wherein:
the aromatic rings are a 6-membered heteroaromatic ring; the aromatic carboxyl group is oriented ortho, meta, or para to the aniline nitrogen; $R_1$ is CH of either R or S configuration; $R_2$ is normal or branched alkyl or fluoroalkyl group having 1 to 6 carbons; $R_3$ is methyl; $R_4$ is a hydrogen or a normal or branched alkyl group having 1 to 6 carbons; and X is sulfoxide.

4. A non-naturally occurring compound comprising at least one methyl sulfoxide moiety, or a pharmaceutically acceptable salt thereof, said compound having formula 8, or a pharmaceutically acceptable salt thereof:

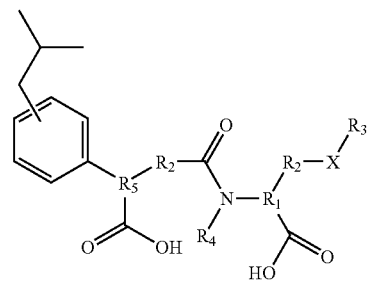

8 wherein:
the aromatic rings are a 6-membered heteroaromatic ring; the sec-butyl group is oriented ortho, meta, or para to the methionine-based moiety; $R_1$ is CH of either R or S configuration; $R_2$ is a normal or branched alkyl or fluoroalkyl group having 1 to 6 carbons; $R_3$ is methyl; $R_4$ is a hydrogen or a normal or branched alkyl group having 1 to 6 carbons; $R_5$ is a CH of either R or S configuration; X is sulfoxide.

5. A non-naturally occurring compound comprising at least one methyl sulfoxide moiety, or a pharmaceutically acceptable salt thereof, said compound having formula 9, or a pharmaceutically acceptable salt thereof:

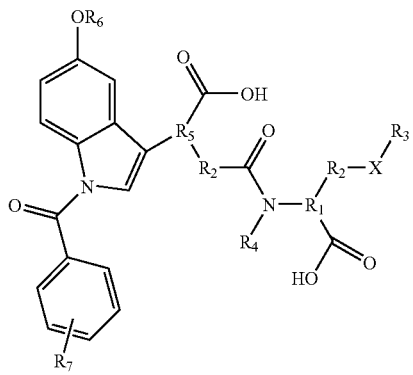

9 wherein:
Groups $R_1, R_2, R_3, R_4, R_5, R_6, R_7$ and X in general structure 9 are defined as follows:
$R_1$ is CH of either R or S configuration; $R_2$ is a normal or branched alkyl or fluoroalkyl group having 1 to 6 carbons; $R_3$ is methyl;
$R_4$ is a hydrogen or a normal or branched alkyl group having 1 to 6 carbons; $R_5$ is a CH of either R or S configuration; $R_6$ is a hydrogen or a normal or branched alkyl or fluoroalkyl group having 1 to 6 carbons; $R_7$ is any halogen oriented ortho, meta, or para to the carbonyl group, and X is S or Se in any oxidation state.

6. A non-naturally occurring compound comprising at least one methyl sulfoxide moiety, or a pharmaceutically acceptable salt thereof, said compound having formula 9a, or a pharmaceutically acceptable salt thereof:

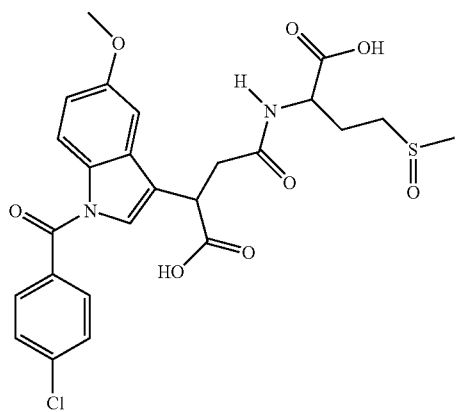

9a

7. A compound having formula 10, or a pharmaceutically acceptable salt thereof:

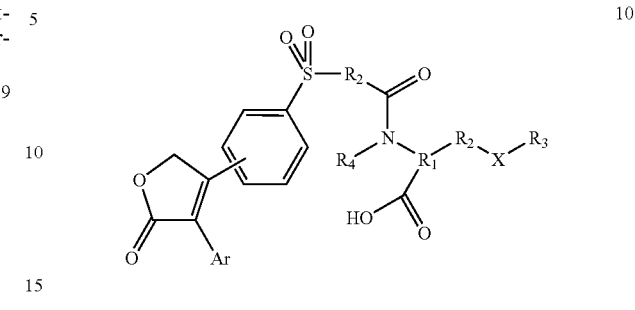

10 wherein:
the lactone ring is oriented ortho, meta, or para to the sulfonyl group; $R_1$ is CH of either R or S configuration; $R_4$ is a normal or branched alkyl or fluoroalkyl group having 1 to 6 carbons; $R_3$ is methyl; $R_1$ is a hydrogen or a normal or branched alkyl group having 1 to 6 carbons; X is S or Se in any oxidation state; Ar is a phenyl, alkyl, halogen substituted phenyl, or heteroaromatic compound.

8. A compound having formula 10a, or a pharmaceutically acceptable salt thereof:

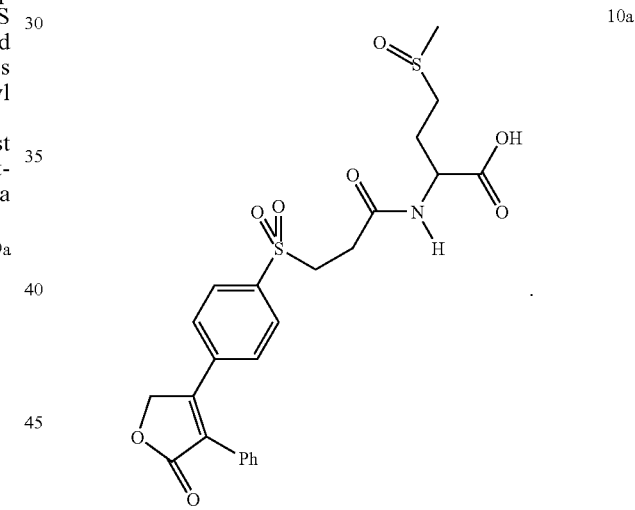

10a

9. A composition comprising the compound of any one of claims 2, 3, 4, 5, and 6 and a pharmaceutically acceptable carrier.

* * * * *